(12) United States Patent
Ziegler et al.

(10) Patent No.: US 12,280,204 B2
(45) Date of Patent: Apr. 22, 2025

(54) METHOD FOR MEASURING FLOW FEATURES IN AN INHALER, INHALER AND SYSTEM

(71) Applicant: Novartis AG, Basel (CH)

(72) Inventors: Dominik Ziegler, Basel (CH); Richard Pavkov, East Hanover, NJ (US)

(73) Assignee: Novartis AG, Basel (CH)

( * ) Notice: Subject to any disclaimer, the term of this patent is extended or adjusted under 35 U.S.C. 154(b) by 232 days.

(21) Appl. No.: 16/073,348

(22) PCT Filed: Jan. 23, 2017

(86) PCT No.: PCT/EP2017/051323
§ 371 (c)(1),
(2) Date: Jul. 27, 2018

(87) PCT Pub. No.: WO2017/129521
PCT Pub. Date: Aug. 3, 2017

(65) Prior Publication Data
US 2019/0030262 A1    Jan. 31, 2019

(30) Foreign Application Priority Data
Jan. 28, 2016   (EP) .................................... 16153186

(51) Int. Cl.
*A61M 15/00*     (2006.01)
*A61M 16/00*     (2006.01)

(52) U.S. Cl.
CPC ...... *A61M 15/0001* (2014.02); *A61M 15/003* (2014.02); *A61M 15/008* (2014.02);
(Continued)

(58) Field of Classification Search
CPC .............. A61M 15/003; A61M 15/008; A61M 2205/3334; A61M 2205/43
See application file for complete search history.

(56) References Cited

U.S. PATENT DOCUMENTS 6,178,302 B1    1/2001   Nagashima
6,958,691 B1   10/2005   Anderson
(Continued)

FOREIGN PATENT DOCUMENTS

EP     2686049 B1    4/2015
EP     2859906       4/2015
(Continued)

OTHER PUBLICATIONS

Holmes, "A Method of Estimating Inspiratory Flow Rate and Volume from an Inhaler Using Acoustic Measurements" *Physiological Measurements* 34:903-914, 2013.
(Continued)

*Primary Examiner* — Joseph D. Boecker
*Assistant Examiner* — Thomas W Greig
(74) *Attorney, Agent, or Firm* — Frost Brown Todd LLP

(57) ABSTRACT

The present invention relates to a method for measuring at least one inhalation flow feature in an inhaler, wherein a capsule containing a formulation is located in the inhaler, the method comprising the steps of sensing an impact feature relating to impacts of the capsule on the inhaler and correlating the impact feature to at least one inhalation flow feature. The present invention also relates to an inhaler adapted to aerosolize a formulation contained in a capsule, wherein the inhaler comprises a sensor for sensing an impact feature relating to impacts of the capsule on the inhaler and a processor for correlating the impact feature to at least one inhalation flow feature. The present invention also relates to a system comprising an inhaler adapted to aerosolize a formulation contained in a capsule and a computing device external of the inhaler, wherein the inhaler comprises a sensor for sensing an impact feature relating to impacts of the capsule on the inhaler and a data-receiving-transmitting means to receive and transmit data from and to the external
(Continued)

computing device, wherein the external computing device also comprises data-receiving-transmitting means to receive and transmit data from and to the inhaler, wherein the inhaler and/or the external computing device comprises processing means for correlating the impact feature to at least one inhalation flow feature.

17 Claims, 16 Drawing Sheets

(52) U.S. Cl.
CPC . *A61M 16/0003* (2014.02); *A61M 2205/3331* (2013.01); *A61M 2205/3576* (2013.01)

(56) References Cited

U.S. PATENT DOCUMENTS

| | | | |
|---|---|---|---|
| 7,151,456 B2 | 12/2006 | Godfrey | |
| 7,191,777 B2 | 3/2007 | Brand | |
| 7,721,730 B2 | 5/2010 | Hamano | |
| 8,251,914 B2 * | 8/2012 | Daniels | A61B 5/083 600/529 |
| 8,424,517 B2 * | 4/2013 | Sutherland | A61M 15/008 128/200.14 |
| 8,474,452 B2 | 7/2013 | Matter | |
| 8,479,730 B2 | 7/2013 | Ziegler | |
| 8,622,241 B2 | 1/2014 | Geboers | |
| 8,807,131 B1 | 8/2014 | Tunnell | |
| 9,016,147 B2 | 4/2015 | Adamo | |
| 9,242,056 B2 | 1/2016 | Andersen | |
| 9,390,457 B2 | 7/2016 | Baym | |
| 9,555,200 B2 * | 1/2017 | Hosemann | A61M 15/0041 |
| 9,744,319 B2 | 8/2017 | Denyer | |
| 10,029,056 B2 | 7/2018 | Anderson | |
| 10,463,816 B2 * | 11/2019 | Calderon Oliveras | A61M 15/008 |
| 2002/0189615 A1 | 12/2002 | Henry | |
| 2003/0074223 A1 | 4/2003 | Hickle | |
| 2004/0025877 A1 | 2/2004 | Crowder | |
| 2005/0087473 A1 | 4/2005 | Fabricius | |
| 2008/0110452 A1 | 5/2008 | Kotnik | |
| 2009/0308387 A1 * | 12/2009 | Andersen | A61M 15/00 128/203.15 |
| 2010/0097380 A1 * | 4/2010 | Daniels | A61B 5/087 345/440.2 |
| 2011/0298587 A1 | 12/2011 | Walz | |
| 2012/0003928 A1 | 1/2012 | Tsvey | |
| 2012/0247235 A1 | 10/2012 | Adamo | |
| 2013/0146613 A1 | 6/2013 | Balthes | |
| 2013/0151162 A1 | 6/2013 | Harris | |
| 2014/0000603 A1 * | 1/2014 | Hosemann | A61M 15/0035 128/203.21 |
| 2014/0106324 A1 | 4/2014 | Adams | |
| 2014/0182854 A1 | 7/2014 | Mukhopadhyay | |
| 2015/0174349 A1 | 6/2015 | Tunnell | |
| 2015/0196724 A1 * | 7/2015 | Adamo | A61K 9/0075 128/203.14 |
| 2015/0196728 A1 | 7/2015 | Aldana | |
| 2016/0081651 A1 * | 3/2016 | Nam | A61B 7/003 600/529 |
| 2016/0256639 A1 | 9/2016 | Sickle | |

FOREIGN PATENT DOCUMENTS

| | | |
|---|---|---|
| EP | 3199193 A1 | 8/2017 |
| EP | 3407945 B1 | 5/2022 |
| JP | 2006153760 A | 6/2006 |
| JP | 2010-160230 A2 | 7/2010 |
| JP | A-2011-174788 | 9/2011 |
| RU | 2372105 C2 | 11/2009 |
| WO | WO 1992/017231 | 10/1992 |
| WO | WO 2003/020349 | 8/2002 |
| WO | WO 2005/113042 | 12/2005 |
| WO | WO 2007/101438 | 9/2007 |
| WO | WO 2010/066456 | 6/2010 |
| WO | WO2011/056889 | 5/2011 |
| WO | WO 2011/130583 | 10/2011 |
| WO | WO2012/123448 | 9/2012 |
| WO | 2013016784 A1 | 2/2013 |
| WO | WO 2014/033229 | 3/2014 |
| WO | WO 2014/204511 | 12/2014 |
| WO | 2015127258 | 8/2015 |

OTHER PUBLICATIONS

Coates, "Influence of air flow on the performance of a dry powder inhaler using computational and experimental analyses" Pharm Res. 22(9):1445-53, Sep. 2005.
Coates, "The role of capsule on the performance of a dry powder inhaler using computational and experimental analyses" 22(6):923-932 Jun. 2005.
BR Examination Report—May 12, 2020—No. BR112017028579-7.
CNIPA examination report Mar. 9, 2020 No. 201680046268.6.
EPO Examination Report—Apr. 3, 2020—No. 15175216.9.
EPO Examination Report—Aug. 7, 2018—No. 15175216.9.
EPO Examination Report—Jul. 20, 2020—No. 16741882.1.
EPO Search Report—Sep. 24, 2015—No. 15 175216.9.
JP Office Action Mar. 3, 2019—No. 2017-567301 (English translation).
Official Action—Jan. 31, 2019 RU No. 2018103754/14.
Search Report—Jan. 29, 2019 RU No. 2018103754/14.
Search Report and Written Opinion PCT/EP2016/051389.
US PTO Notice of References Cited for U.S. Appl. No. 15/545,375, dated Oct. 14, 2020.
Flume, PA et al. "Optimising inhaled mannitol for cystic fibrosis in an adult population." Breathe (Sheff). Mar. 2015, 11(1), pp. 39-48. Supplemental video "Inhalation technique" downloadable from "https://breathe.ersjournals.com/content/11/1/13.figures-only" Date of publication unknown, link and screenshots provided.
Rau, Joseph L., "Practical Problems With Aerosol Therapy in COPD" Special Articles, Respiratory Care, Feb. 2006, vol. 51, No. 2, pp. 158-172.
Rx Files, "COPD New Drugs, New Devices and Considerations for Best Practice" Sep. 2015, author unknown.
Notice of Opposition to European Patent EP3407945, Application No./Patent No. 17704675.2-1122/3407945, by Kilburn & Strode LLP, filed Feb. 10, 2023.
Statement of Ground for Appeal for Eurpean Patent No. EP3199193 by Kilburn & Strode LLP, filed Apr. 21, 2023.
U.S. Appl. No. 15/741,630.
U.S. Appl. No. 17/499,488.
U.S. Appl. No. 15/545,375.

\* cited by examiner

METHOD FOR MEASURING FLOW FEATURES IN AN INHALER, INHALER AND SYSTEM

The present invention relates to inhalers. In particular, the present invention relates to a method for measuring flow features of a flow supplied to an inhaler, a corresponding inhaler and a corresponding system.

Inhalers are known, e.g., from WO 2005/113042 A1. This document discloses an inhaler having a chamber into which a capsule containing a formulation can be placed. Once the capsule is placed in the inhaler, the inhaler may be closed. The capsule may be pierced by respective needles. A user may then place the mouthpiece of the inhaler in his/her mouth and inhale. This creates an airflow which makes the capsule spin in the chamber to release the formulation to the user.

In such a configuration, it would be desirable to obtain information about the user's breath, i.e. about features of the user's inhalation. Such features may include, e.g., the duration of inhalation, the overall inhalation volume, the maximum volume flow during the inhalation and the volume flow profile. By means of such features of the user's inhalation, the inhalation efficacy may be assessed, i.e. it may be assessed whether the inhaler has been used in such a manner that the formulation has been aerosolized sufficiently.

In light of the above, it is an object of the present invention to provide a method to obtain features of the user's inhalation, particularly in a capsule based inhaler. It is also an object of the present invention to provide a corresponding inhaler and a corresponding system.

These objects are fulfilled by the method for measuring at least one inhalation flow feature, the inhaler and the system of the present invention.

According to a first aspect, the present technology pertains to a method for measuring at least one inhalation flow feature in an inhaler. A capsule containing a formulation is located in the inhaler. In particular, the formulation may be a pharmaceutical formulation. A capsule relates to a container allowed to move freely (e.g., spin) when located in the inhaler. The method comprises the steps of sensing an impact feature relating to impacts of the capsule on the inhaler and correlating the impact feature to at least one inhalation flow feature. In other words, the capsule may be effected to spin in the inhaler. Such a spinning may in particular be effected after the capsule has been opened. The user may then inhale, which may cause the capsule to spin and to release its formulation. When spinning, the capsule impacts on the inhaler, e.g., on inner walls of the inhaler. Such impacts may be sensed by the present method, e.g., by an impact sensor. One non-limiting example is the sound which may be sensed by a microphone. That is, the capsule impacts on the inhaler and causes a sound (an impact feature). The present technology relates this impact feature generated by a spinning capsule to a flow feature, e.g. the instantaneous flow.

Such a method and the corresponding inhaler and system may be advantageous for a plurality of reasons. It allows to get additional information relating to the flow in a convenient fashion and without requiring any extra work from the user. That is, the impact feature (e.g. sound) generated by the spinning capsule is sensed and used as a measure for a flow feature (e.g. instantaneous flow, flow volume).

As discussed, the impact feature may be a sound generated by the impacts of the capsule on the inhaler. Such an impact feature may be sensed easily, e.g., by means of a microphone.

Correlating the impact feature to at least one inhalation flow feature may comprise determining at least one characteristic of the sensed impact feature and relating the at least one characteristic of the sensed impact feature to at least one inhalation flow feature.

The at least one characteristic may comprise a mean value of the impact feature, a peak value of the impact feature and/or a duration of the impact feature above a threshold. Such impact features may be simple to obtain and may allow a convenient and simple derivation of the inhalation flow feature (e.g., instantaneous inhalation flow).

The at least one characteristic may comprise two or three of the characteristics mentioned in the previous paragraph and at least one inhalation flow feature may be determined by a combination of the characteristics. Such a combination of characteristics may yield a more robust and improved result than when only one characteristic is used.

The at least one characteristic may comprise a peak to mean value of the impact feature, a peak count of the impact feature, a variance of the impact feature and/or a kurtosis of the impact feature. Such statistical values of the impact feature may be particularly advantageous to use. The capsule spinning in the inhaler impacts on the inhaler, as discussed. Such impacts may cause distinct signals peaks in the impact feature. It will be appreciated that a capsule impacting on the inhaler will cause a distinct "rattle", that is a peak in the sound signal. That is, a capsule spinning in the inhaler and impacting on the inhaler causes distinct peaks on the signal causing distinct results for the characteristics discussed in this paragraph (peak to mean value, peak count, variance and kurtosis). This is why these characteristics of the impact feature are particularly suitable to derive inhalation flow features from the impacts of a spinning capsule. With particular reference as regards the kurtosis and the variance of the impact feature, reference can also be made to EP 2 686 049 B1, where these characteristics are described to be used for the detection of the presence of a capsule (not, however, for the derivation of a flow feature).

Again, two, three or four of the characteristics discussed in the previous paragraph may be used and the inhalation flow feature (e.g., the instantaneous flow) may be determined by a combination of such characteristics, which may lead to an improved and more robust result.

Correlating the impact feature to at least one inhalation flow feature may comprise dividing the sensed impact feature into time intervals, determining the at least one characteristic of the sensed impact feature for the time intervals and relating the at least one characteristic of the sensed impact feature to a flow for each time interval. The time intervals may have a length in the range of 10 ms to 500 ms, preferably 100 ms to 300 ms and further preferably 150 ms to 250 ms. This may reduce the required data storage requirements, as only a limited number of values need to be stored, which number may be reduced to the situation when the impact feature is continuously sensed and the flow feature, e.g. the flow, is continuously determined. This may allow these steps to be performed by the inhaler itself, without requiring the inhaler to have a sophisticated data processing and data storage means.

The steps of sensing an impact feature and correlating the impact feature to at least one inhalation flow feature with its sub-steps may be performed for a plurality of inhalations, to thereby arrive at a plurality of flows for each time interval, wherein the plurality of flows for each time interval are combined to a combined flow for each time interval. Again, this may render the method more robust. The plurality of inhalations may be at least 3, preferably at least 5 and more preferably at least 10 inhalations.

The at least one inhalation flow feature may comprise at least one of a peak inhalation flow, an inhalation flow duration and an inhalation flow volume. Such inhalation flow features may be stored locally on the inhaler. Such features may be of particular interest to both the user and a practitioner to monitor correct usage of the inhaler. The at least one inhalation flow feature may comprise two or three of the features listed above.

The at least one inhalation flow feature may be displayed on the inhaler. This may provide the user with a direct and convenient feedback as regards correct usage of the inhaler and may therefore improve the user's engagement and compliance and correct usage of the inhaler.

The method may comprise sending data relating to the impact feature or the at least one inhalation flow feature to a device external to the inhaler. In other words, data relating to the impact feature, e.g., the recorded sound, or the at least one inhalation flow feature, e.g., sound parameters, may be sent or "streamed" to an external device, such as a smart phone or other smart device. This may have the advantage that applications ("Apps") can be changed more easily and therefore potential changes and/or updates of the method algorithm would be more straight forward. Furthermore, the data may be used by a practitioner to monitor correct usage of the inhaler and the user's compliance.

The step of correlating the impact feature to at least one inhalation flow feature may be at least partially performed by the external device. As an example, the inhaler may send the discussed data to an external device (e.g., a smart phone, a computer, a tablet or another "smart" device), which external device may then perform subsequent data processing. This may reduce the requirements of potential data processing means on the inhaler, rendering the inhaler relatively simple and cheap.

However, the step of correlating the impact feature to at least one inhalation flow feature may be performed by the inhaler, in case a stand-alone device is desired.

The method may further comprise the step of frequency filtering the impact feature before correlating the impact feature to at least one inhalation flow feature, wherein the filtering preferably prevents signals in the frequency range below 3 kHz and above 15 kHz to pass and further preferably, wherein the filtering prevents signals below 4.5 kHz and above 10 kHz to pass. It has been found that the signals in the described ranges are particularly representative for the impacts generated by the capsule impacting on the inhaler and that by means of the above described frequency filtering, other noises (such as ambient noise and air flow noise) may be filtered out not to compromise the results.

The method may also comprise effecting the capsule to spin in the inhaler and to impact on the inhaler. In particular, this may be done be a user inhaling.

The present technology also pertains to a use of the method above described method, wherein the method is performed at least partially simultaneously with the formulation being supplied to a user of the inhaler. That is, the capsule may be opened and the capsule may release the formulation during spinning.

The present technology also pertains to a use of the method, the use comprising considering the at least one inhalation flow feature to monitor the user's compliance. That is, it may be monitored how consistently an inhaler is used by the user and whether the use is in accordance with a prescription.

The present technology also pertains to a use of the method, the use comprising considering the at least one inhalation flow feature to monitor a health condition of the user. That is, e.g., by means of the peak inhalation flow a user is able to perform, by means of the total inhalation flow volume and its duration, a health condition of the user may be monitored. E.g., a user suffering from asthma may produce different inhalation flow features than a healthy user breathing normally. By means of this use, e.g., the long term development of a health condition and/or a disease may be monitored.

In the uses described in the two preceding paragraphs, the at least one inhalation flow feature may be considered for a plurality of inhalations. Thus, the user's compliance and/or the user's health condition may be monitored over time.

The present technology also pertains to an inhaler. The inhaler is adapted to aerosolize a formulation contained in a capsule and the inhaler comprises a sensor for sensing an impact feature relating to impacts of the capsule on the inhaler and a processor for correlating the impact feature to at least one inhalation flow feature. Such an inhaler has advantages corresponding to the advantages discussed above with regard to the method.

The sensor may be a microphone. The microphone (or more generally: the sensor) may be fixedly or permanently mounted to the inhaler, i.e. a user may not be able to separate the sensor from the inhaler without breaking the connection between the two. The processor of the inhaler may be adapted to carry out any of the steps relating to data processing and/or correlating the impact feature to at least one inhalation flow feature as discussed above. That is, any of the calculations discussed above may be carried out by the data processing means.

The inhaler may comprise a data-receiving-transmitting means to receive and transmit data from and to an external device, e.g. to an external smart device.

The present technology also pertains to a system comprising an inhaler adapted to aerosolize a formulation contained in a capsule and a computing device external of the inhaler, wherein the inhaler comprises a sensor for sensing an impact feature relating to impacts of the capsule on the inhaler and a data-receiving-transmitting means to receive and transmit data from and to the external computing device, wherein the external computing device also comprises data-receiving-transmitting means to receive and transmit data from and to the inhaler, wherein the inhaler and/or the external computing device comprises processing means for correlating the impact feature to at least one inhalation flow feature.

Again, the sensor may be a microphone.

The processing means may adapted to carry out any of the data processing steps set out above.

Such a method, inhaler and system allow flow features to be conveniently monitored by means of the impacts generated by a capsule spinning inside the inhaler. Thus, they fulfill the objects of the present invention.

Embodiments of the present invention will now be described with reference to the accompanying drawings in which FIG. 1 shows an inhaler;

Figure 3A:
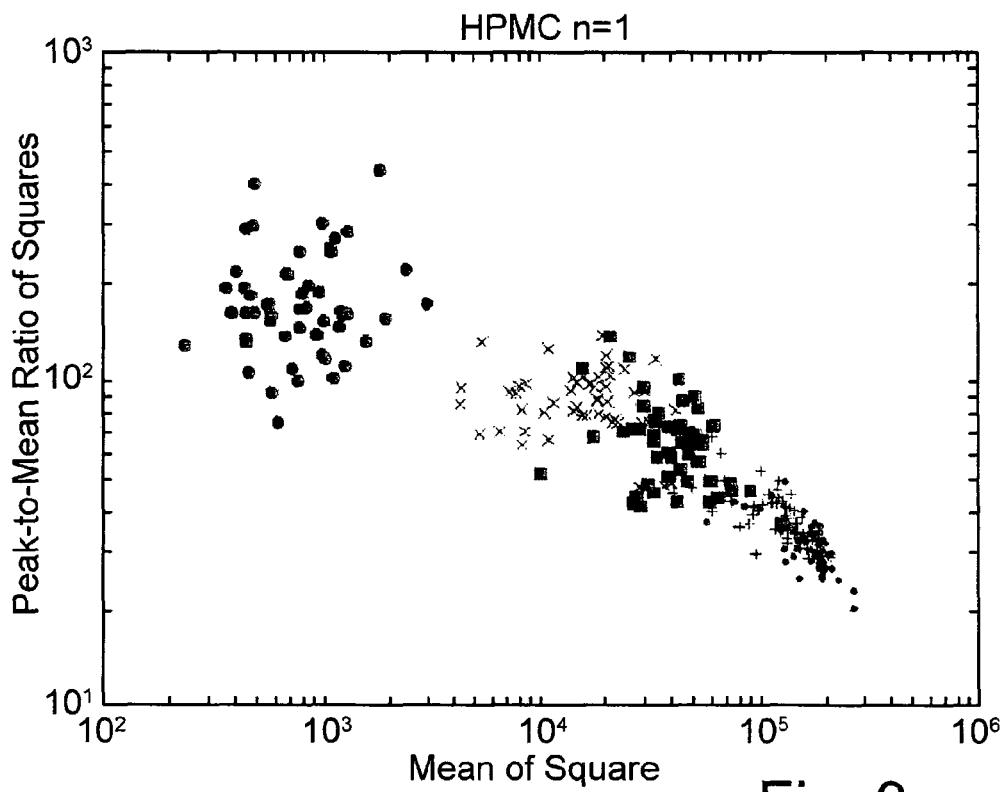
FIGS. 3a to 3h show scatter graphs of the detected mean of square and peak-to-mean ratios of sound detected for different flows.
Figure 3B:
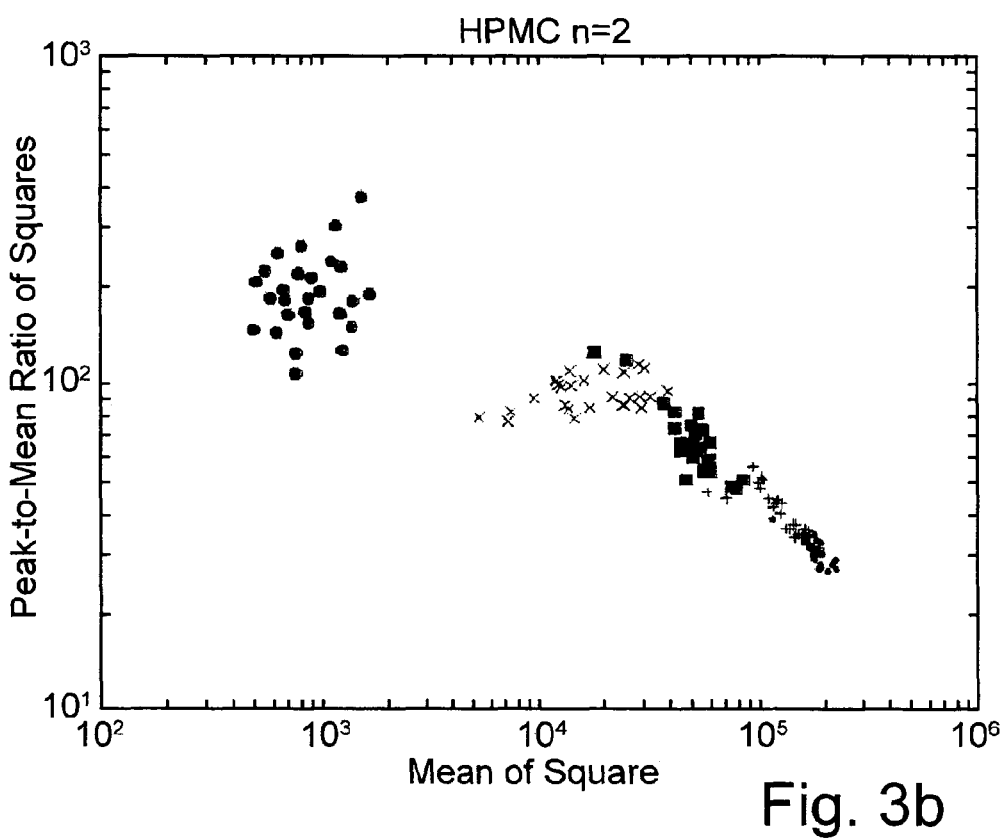
Figure 3C:
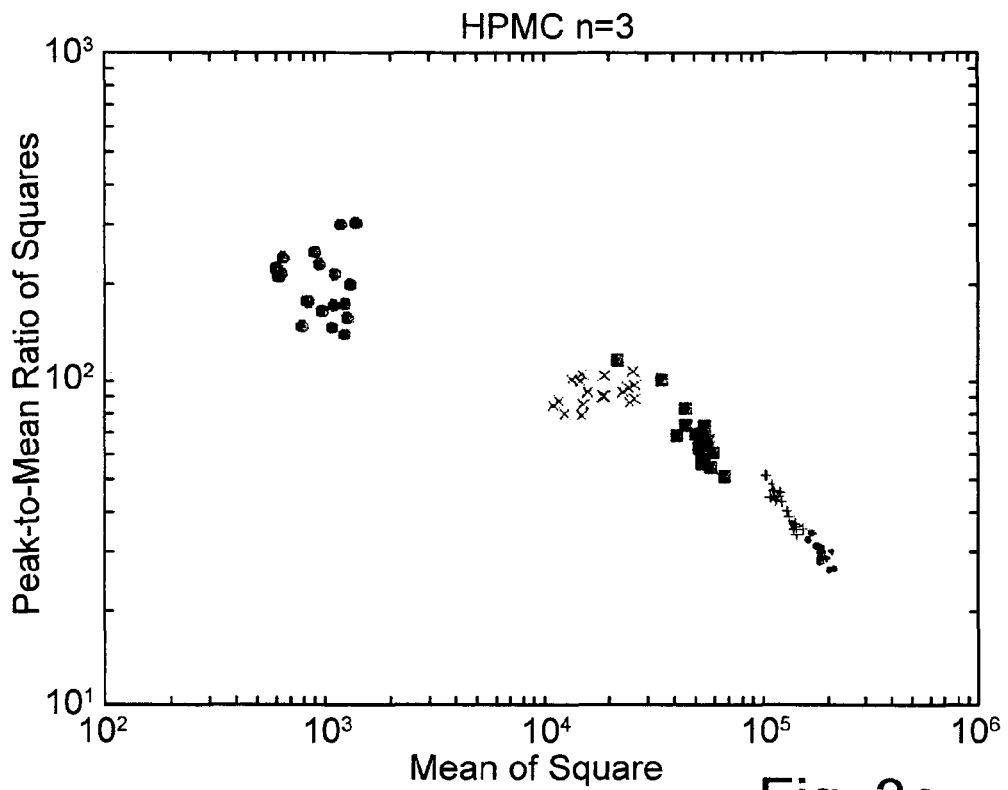
Figure 3D:
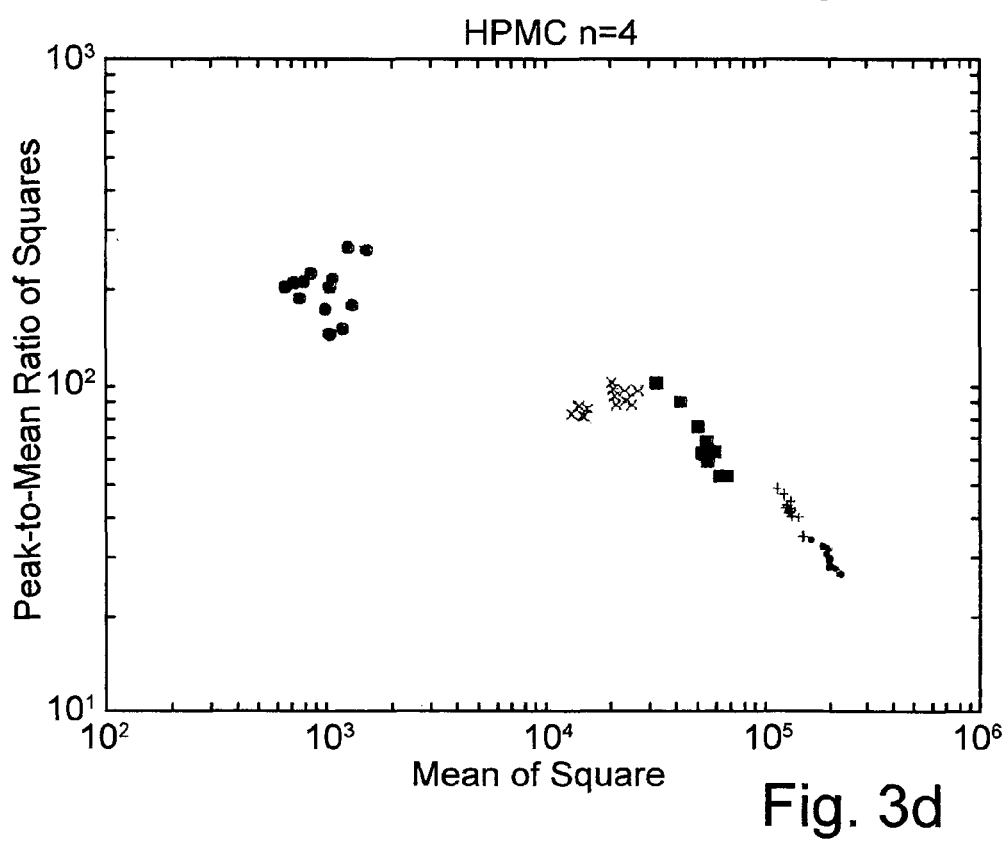
Figure 3E:
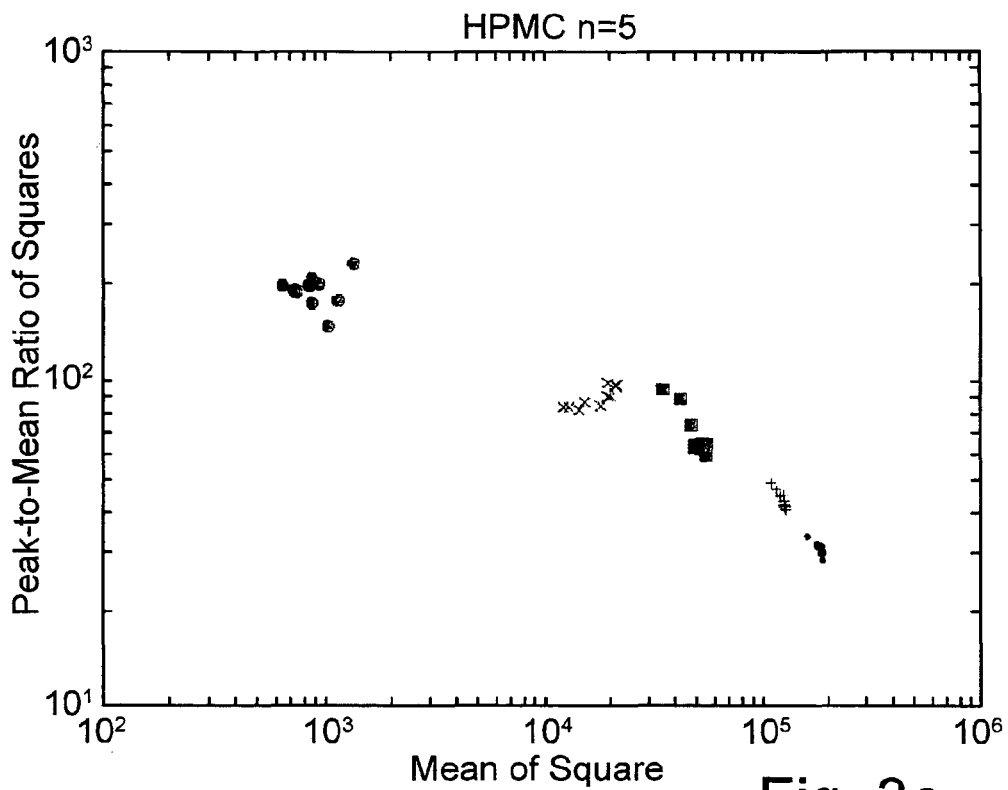
Figure 3F:
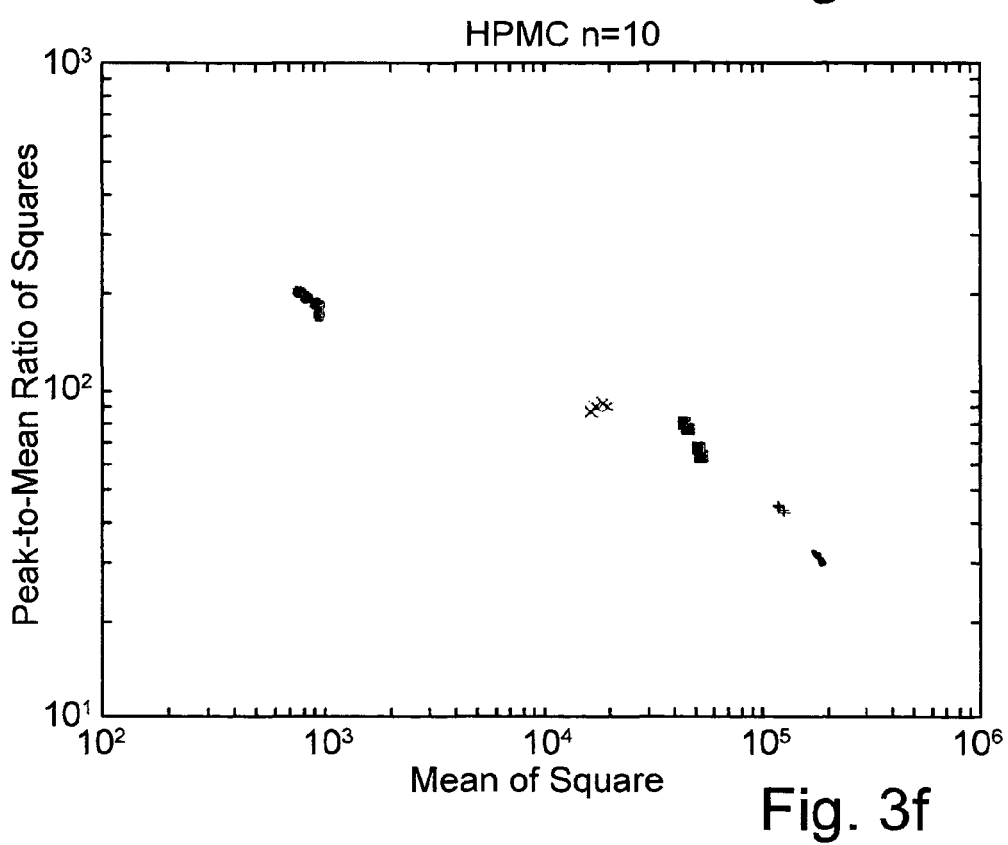
Figure 3G:
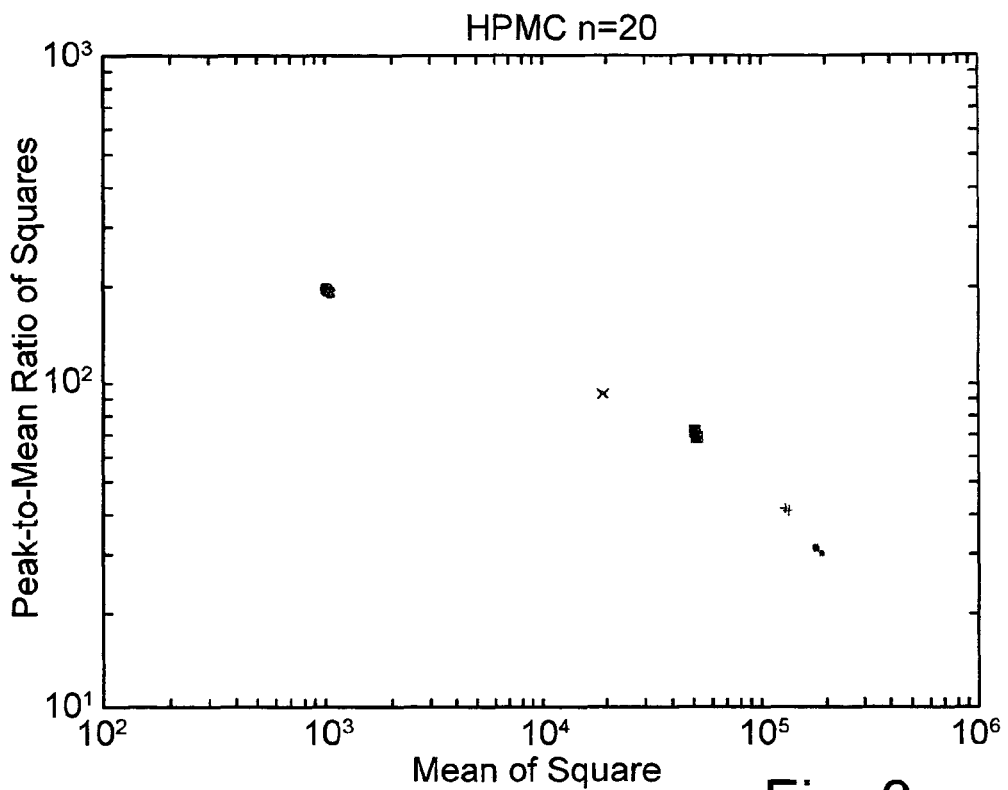
Figure 3H:
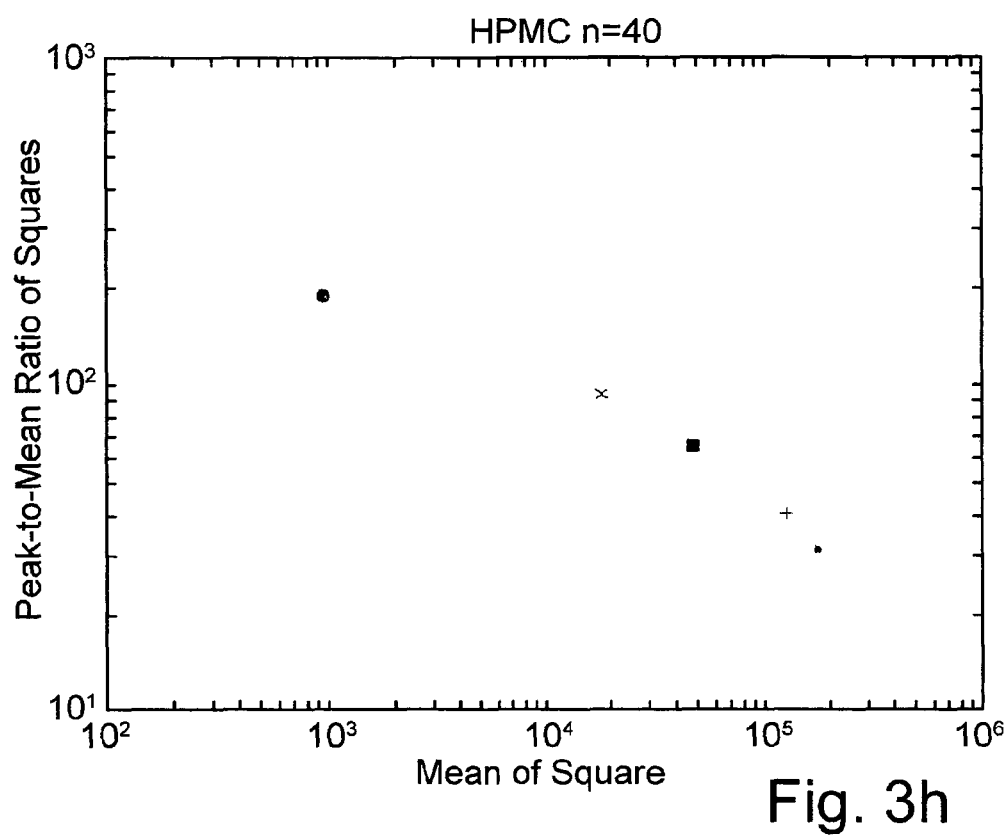
Figure 3I:
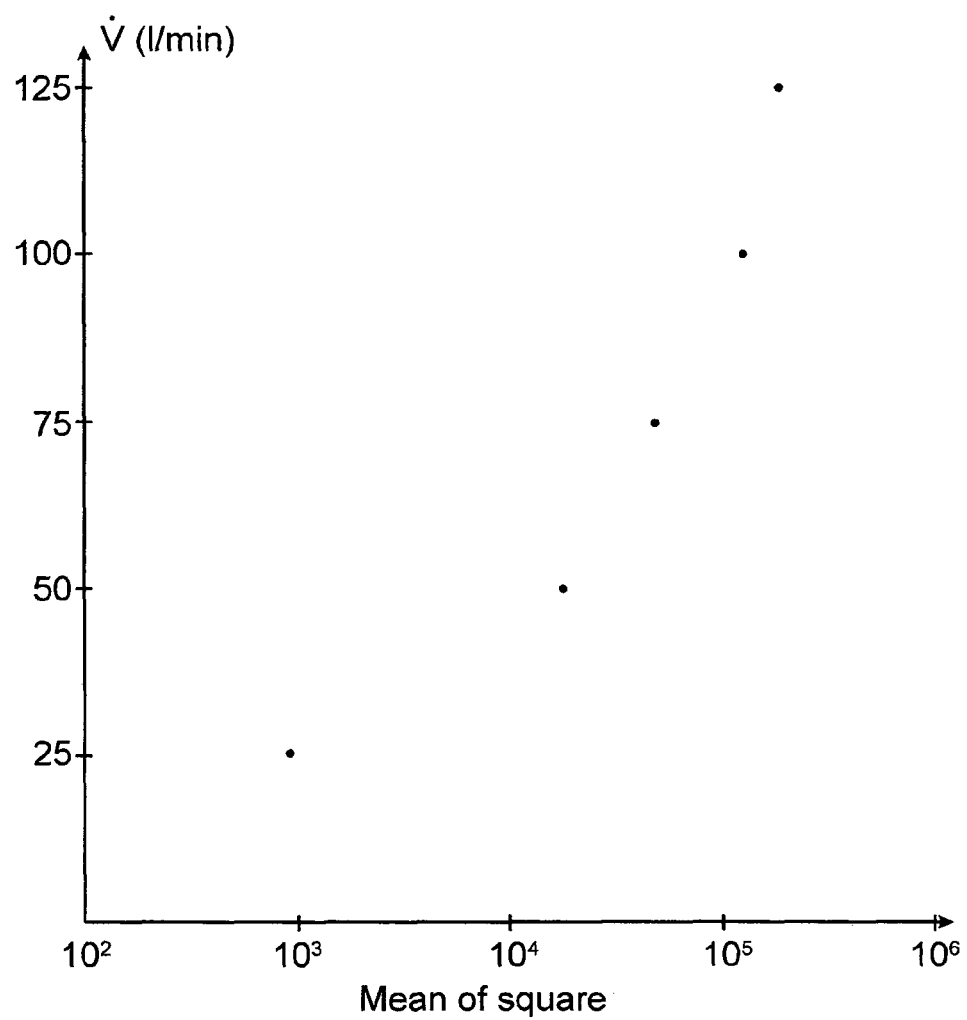
FIGS. 3i and 3j show graphs relating mean of square and peak-to-mean ratios of detected sound to volume flows.
Figure 3J:
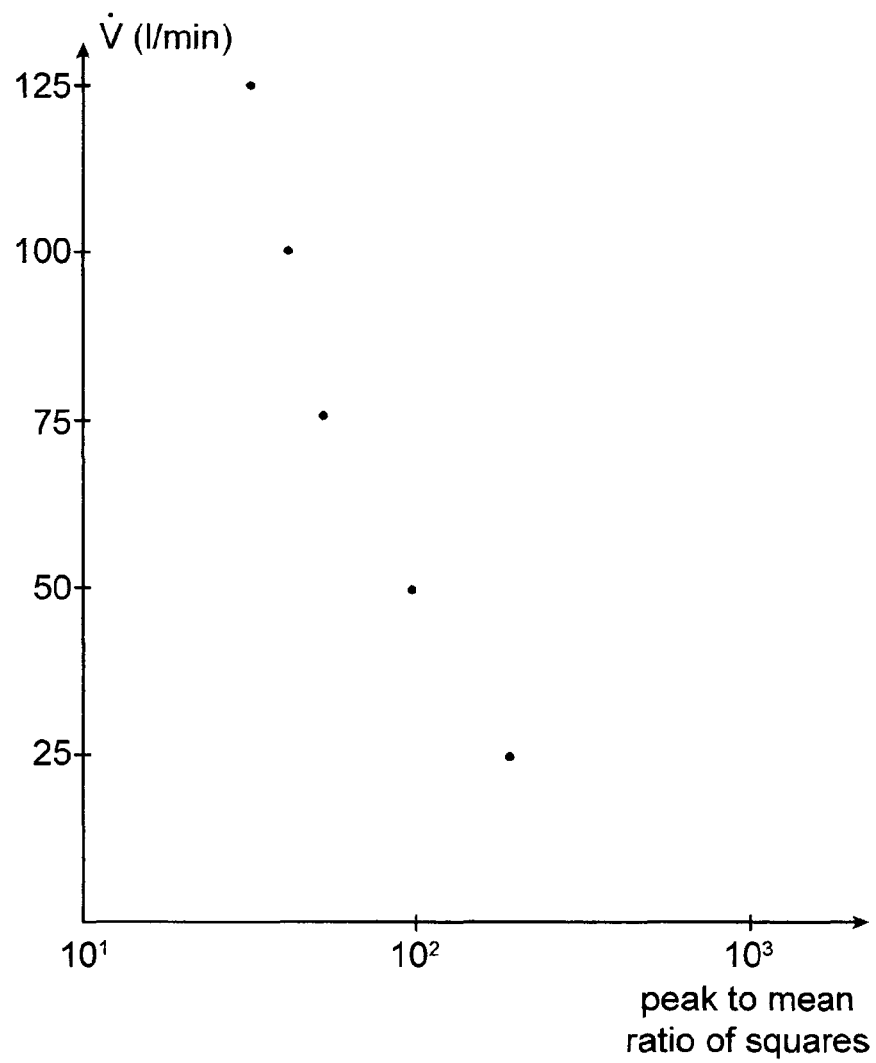
Figure 4A:
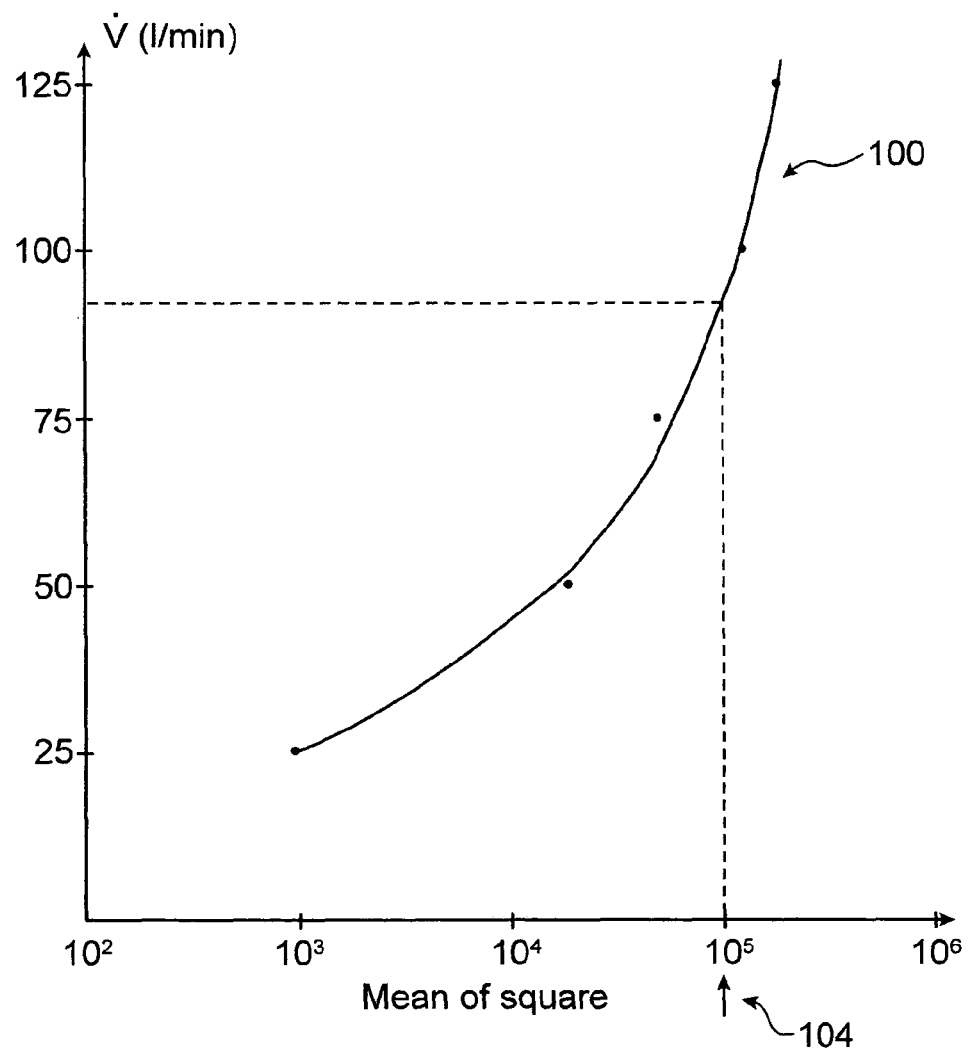
Figure 4B:
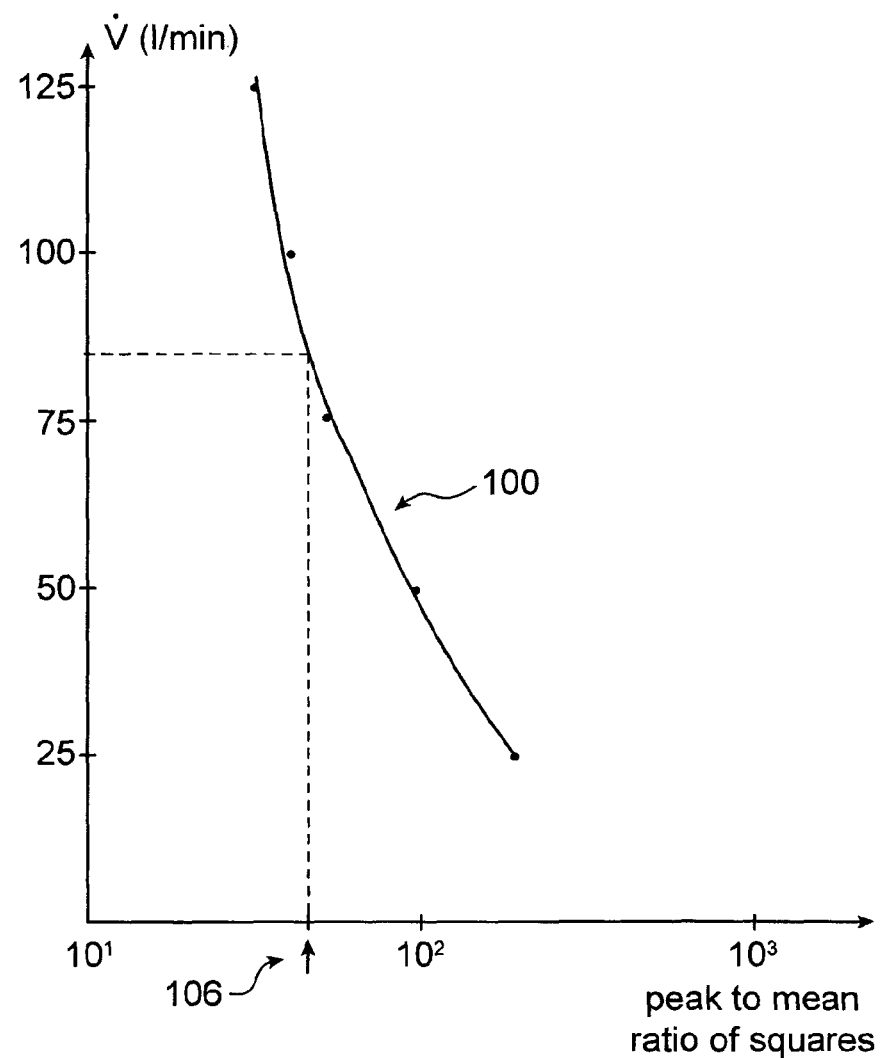
Figure 5:
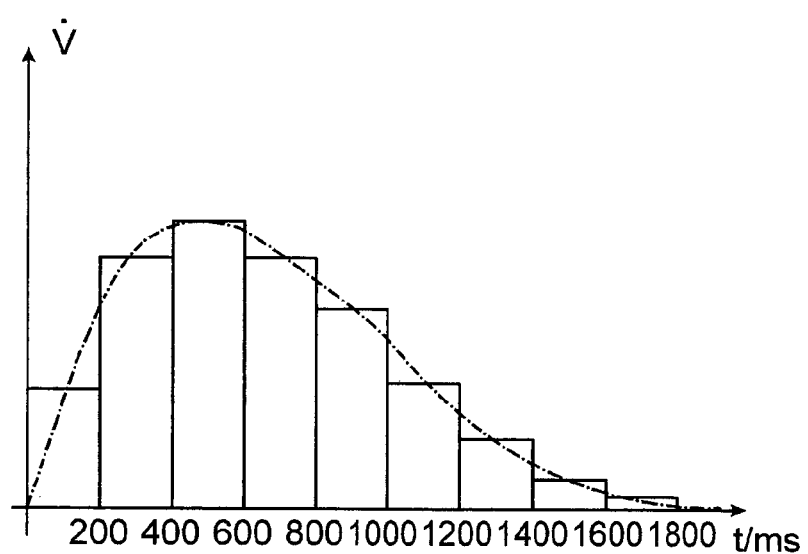
Figure 6:
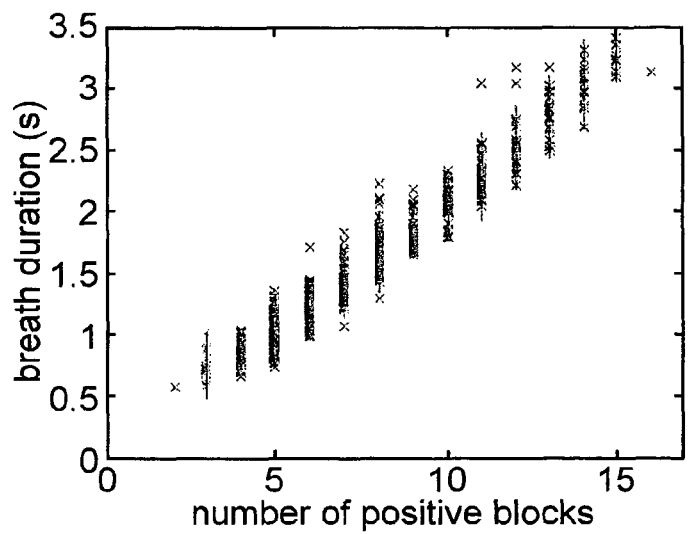
Figure 10:
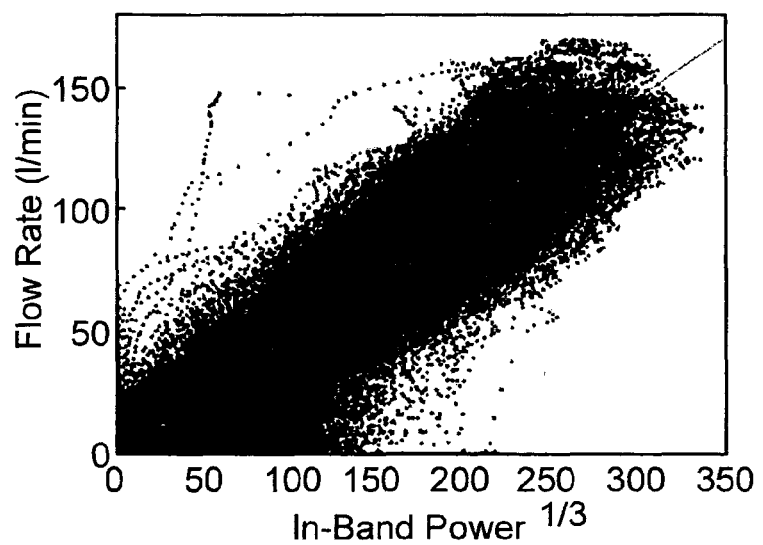
Figure 11:
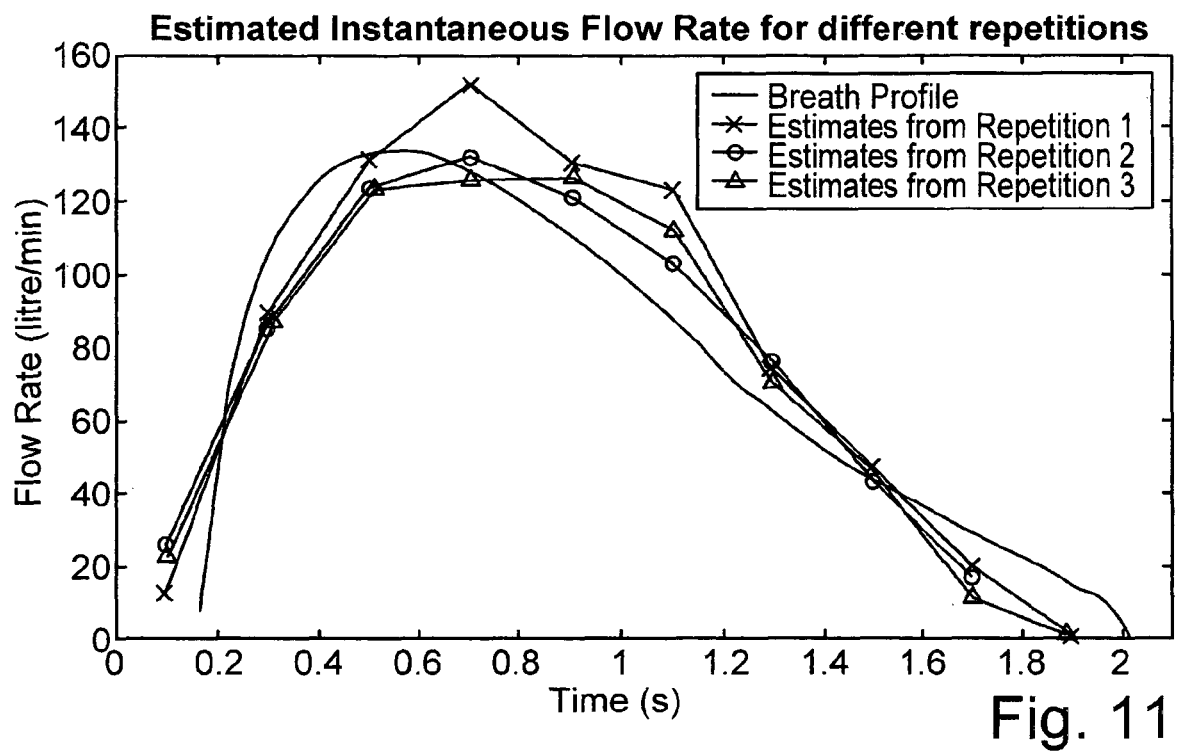
Figure 9A:
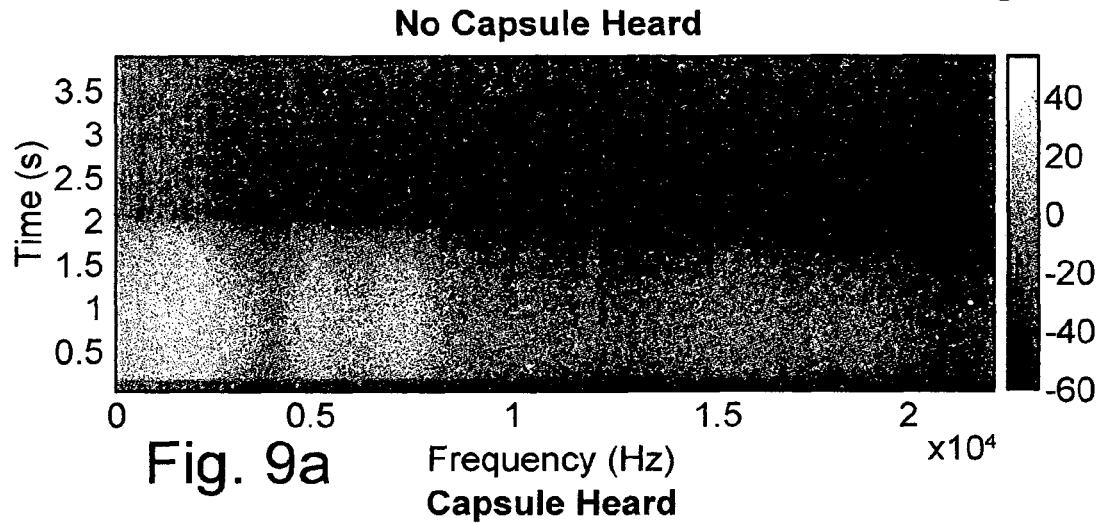
Figure 9B:
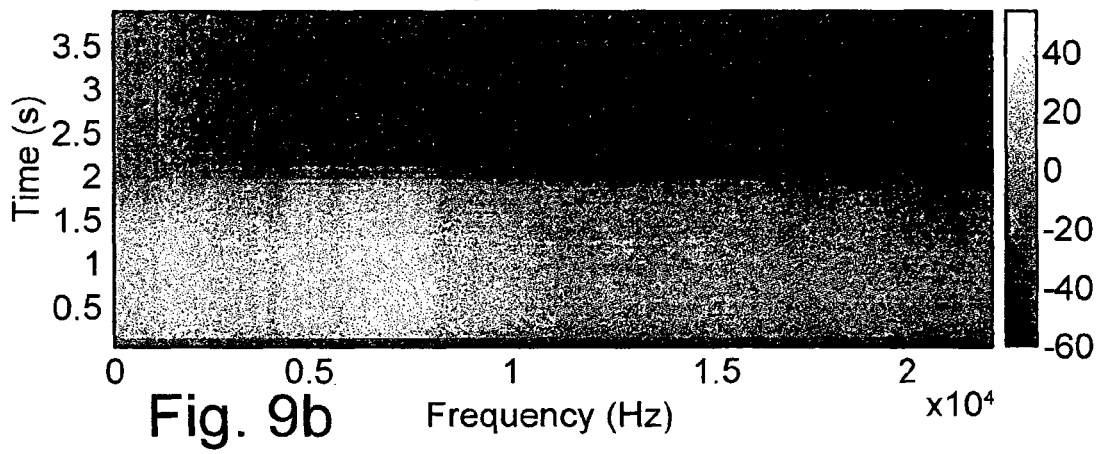
Figure 12:
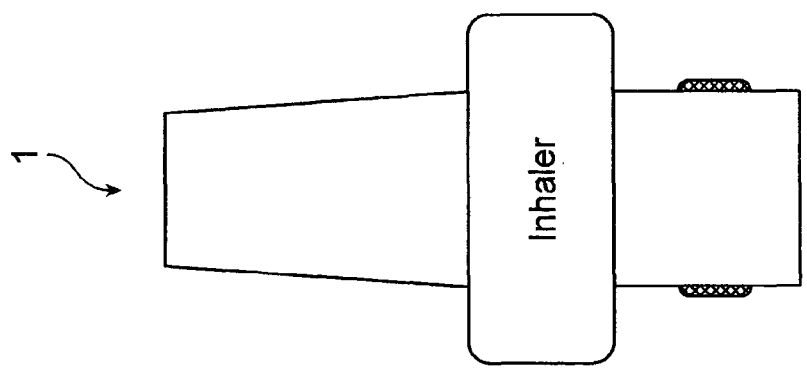
Figure 12:
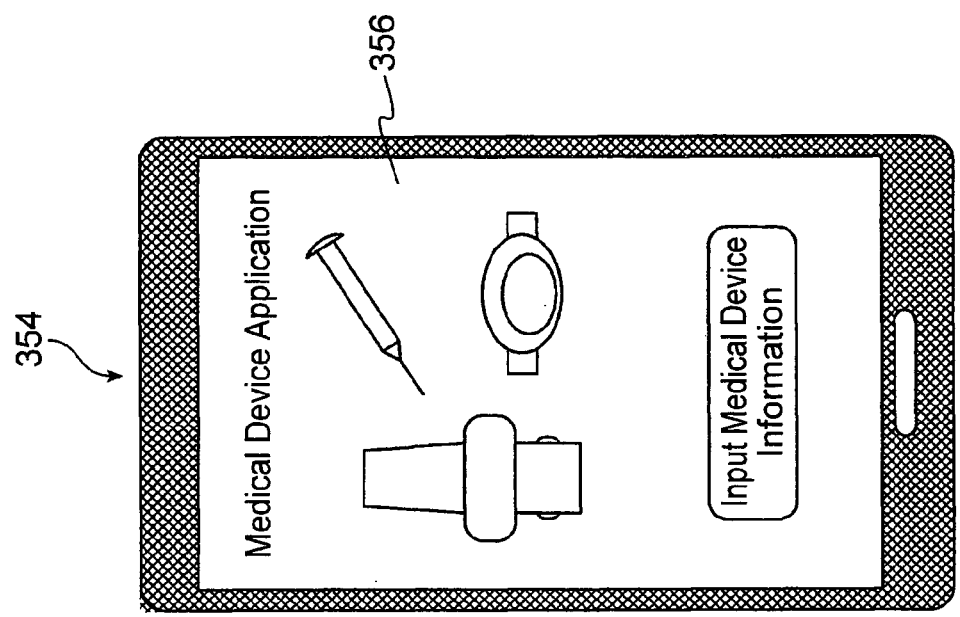

FIGS. 4a and 4b correspond to FIGS. 3i and 3j and depict respective best fit lines;

FIG. 5 shows a graph depicting the determined and real volume flow profile of a user inhaling;

FIG. 6 shows a graph depicting the actual breath or inhaling duration vs. the number of representative 200 ms blocks of sound exceeding a signal threshold;

FIGS. 7a to 7d show graphs depicting the inhalation peak flow vs. different characteristics of the sound;

FIGS. 8a to 8d show graphs depicting the inhalation volume vs. different characteristics of the sound;

FIG. 9 shows graphs depicting spectrograms depicting the sound signal power vs. time and frequency;

FIG. 10 shows a graph depicting an instantaneous flow rate vs. the third root of the sound signal;

FIG. 11 shows an actual flow rate and three flow rates estimated with the present technology vs. time; and FIG. 12 shows a system comprising an inhaler and an external computing device.

Figure 13:
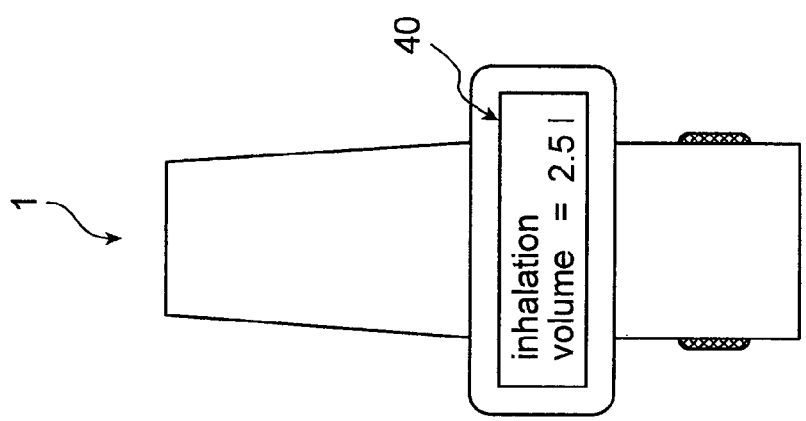

FIG. 13 shows an inhaler with a display.

Figure 1:
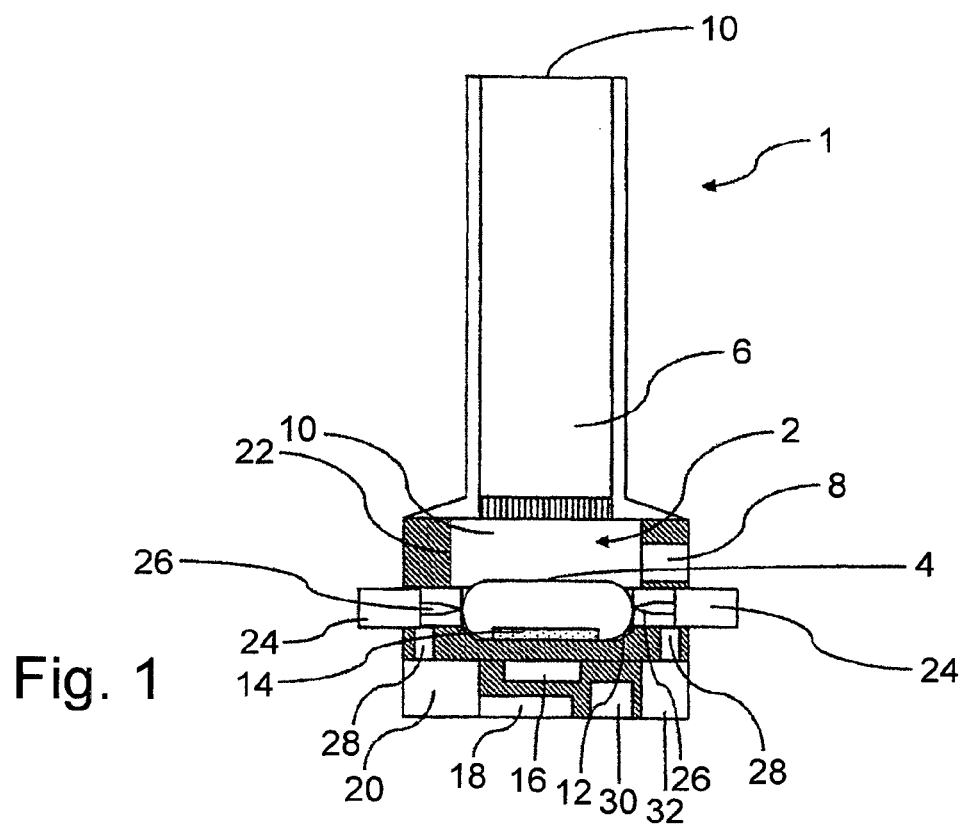

FIG. 1 shows an inhaler 1 (which may be an aerosolizer) comprising a capsule housing 2 containing a medicament capsule 4. The inhaler 1 comprises an airflow path 6 through which air flows during an airflow event. The airflow path 6 extends from at least one air inlet 8 to an outlet 10 and passes through the capsule housing 2. The inlet 8 enters the capsule housing 2 away from a centreline. In this example a top part 10 of the capsule housing 2 is substantially cylindrical and the air inlet 8 enters substantially tangentially to the capsule housing 2 to encourage the air to swirl within the capsule housing 2. The top part 10 of the capsule housing 2 is substantially cylindrical in shape with a diameter longer than a capsule 4 contained therein and a height greater than the diameter of the capsule, but less than the length of the capsule 4. The capsule housing 2 includes a bottom part 12, or coffin, in which the capsule 4 initially rests. The capsule 4 contains a dry powder medicament formulation 14.

The inhaler 1 further comprises a sensor 16, in this case a microphone, located adjacent the bottom part 12 of the capsule housing 2. The sensor 16 is coupled to a processor 18 which is powered by a power source 20, in this case a battery.

The capsule housing 2 is defined by at least one wall 22 and is configured such that when a capsule 4 is located in the capsule housing 2 and sufficient air flows along the airflow path 6, the capsule 4 is drawn into the top part 10 of the capsule housing 2 and spins in the airflow. As the capsule 4 spins it makes repeated impacts on the wall 22 and the sensor 16 is arranged so that it is able to detect these impacts within the capsule housing 2. The sensor 16 generates a signal indicative of the impacts. The processor 18 receives the signal from the sensor 16.

The inhaler 1 also includes a pair of actuator buttons 24 which are coupled to piercing members 26. The buttons 24 can be pressed by a user to cause the piercing members 26 to pierce holes in the ends of a capsule 4 arranged in the bottom part 12 of the capsule housing 2. There are actuations sensors 28 that can generate actuation signals indicative of whether the actuator button 24 has been pressed or not.

The processor 18 receives the signals from the sensors 16, 28 and produces an output signal which may be indicative of one or more of the presence of a capsule during an airflow event, the actuation of the actuation buttons 24, the correct use of the inhaler (correct sequence and timing of the actuation and a capsule being present during an airflow event). The output from the processor 18 and/or the raw output from the sensors are stored in a memory 30 and can be accessed using an output 32, in this case a wireless transmitter.

Figure 2:
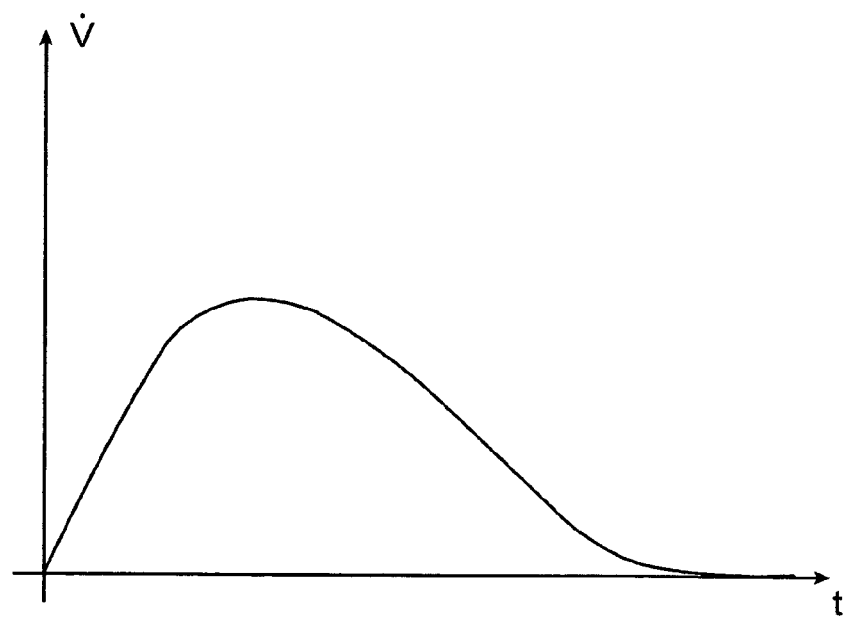
FIG. 2 shows an exemplary graph depicting the volume flow of user inhaling from an inhaler.

As discussed, it is an object of the present invention to obtain information regarding breathing of the user of the inhaler 1, i.e. information about flow characteristics. An exemplary flow graph (depicting volume flow V* vs. time t) is shown in FIG. 2 for one half-breath, i.e. for a user of the inhaler 1 inhaling. Retrieving such information about the breath, i.e. length of inhaling, maximum volume flow, total inhaling volume may be of interest, e.g. to determine how efficiently the inhaler 1 has been used. Furthermore, this also allows trending and coaching of the patient.

The invention uses the noises generated by the spinning capsule 4 to retrieve information about the volume flow, i.e. the user's breath. These noises (also referred to as the sound) are measured by the sensor 16, which here is a microphone. However, other impact sensors may also be used.

It will now be described how the calibration may be performed with reference to FIGS. 3a to 3h. To calibrate the inhaler 1, the inhaler 1 is supplied with a controlled flow, i.e. a flow having a predetermined volume flow, e.g. a volume flow of 25 l/min, 50 l/min, 75 l/min, 100 l/min or 125 l/min. To do so, a suction source is placed at top part 10 and a predetermined suction is supplied to the airflow path 6 resulting in the predetermined volume flow.

With a predetermined airflow supplied to the inhaler 1, a sound generated by the spinning capsule 1 is measured by means of the sensor 16 (e.g. a microphone, though other impact sensors could be used as well). This results in a sound signal.

The sound signal (i.e. sound vs. time) is split into different time sections (also referred to as sections, intervals or blocks). Each section has a predetermined duration, e.g. 200 ms. Each sound signal section may have different sound characteristics including a mean signal, a peak to mean ratio and peak count.

The mean signal may be the mean sound signal detected in the respective section, i.e. the average signal in this section (alternatively, the signal may also be squared first and the average of this squared signal may be used as the mean signal). In any case, the mean signal is a measure for the average "strength" of the signal within the respective section. Any such mean signal will be referred to as a mean value of the sound.

The peak to mean ratio may be the ratio between the signal peaks and the above described mean signal. The signal peaks may correspond to the instances in which the capsule 1 hits a sidewall of the housing 2 when spinning. Again, either the peak may be compared to the mean signal directly or the squares of the peaks may be compared to the mean of the squares signal. Any such peak to mean signal will be referred to as a peak to mean value of the sound.

Another characteristic may be the count of peaks within the respective time section.

It has been found that the above described characteristics are dependent on the flow present in the inhaler. This is depicted in FIG. 3a. This Fig. depicts a graph having the squared mean signal (in arbitrary units) on the x-coordinate and the ratio between the squared peak signal and the squared mean signal on the y-coordinate. To obtain this graph, a hydroxypropyl methylcellulose capsule (HPMC) has been used and different measurements are depicted for different intervals.

The different measurement points refer to an applied flow of:
- 25 l/min

X 50 l/min

■ 75 l/min

+ 100 l/min

• 125 l/min

Each measurement point in FIG. 3a corresponds to the assessment of the mean of square signal characteristic (on the x-coordinate) and the peak-to-mean characteristic (on the y-coordinate) for intervals of 200 ms. The different symbols represent the different flows supplied to the inhaler.

As can be seen, flow of 25 l/min generates the signals having relatively low mean of square values and relatively large peak-to-mean values. Generally speaking, the higher the flow, the lower the mean of square values and the higher the peak to mean ratios.

Furthermore, as can also be seen from FIG. 3a, the different intervals for the 25 l/min flow supplied to the inhaler do not all yield one and the same result, but they are spread both as regards the mean of square characteristic and the peak-to-mean of square characteristic. The same also applies to the other flows. As can be imagined, this is due to the capsule 4 not always behaving in exactly the same way when subjected to a flow and due to signal noise.

In any case, as can be seen already from FIG. 3a, there is a clear trend that the higher the supplied flow, the lower the mean of square characteristic and the higher the peak-to-mean of squares characteristic.

FIGS. 3b to 3h depict respective graphs, where the number of repetitions has been increased. That is, e.g., FIG. 3b depicts the situation where two repetitions have been performed for each measurement point. That is, every measurement point in FIG. 3b corresponds to the average of two measurement points in FIG. 3a. FIGS. 3c, 3d, 3e, 3f, 3g, and 3h correspond to the combination of 3, 4, 5, 10, 20 and 40 measurement points, respectively.

Again, it is noted that the graph in FIG. 3h relates to information relating the flow supplied to the inhaler 1 (which determines the marking of the measurement points), the mean of the squared sound signals and the peak-to-mean of the squares. As discussed, the measurement point on furthest left and highest corresponds to flow being supplied at 25 l/min and the other measurements correspond to flows (from left to right) of 50, 75, 100 and 125 l/min, respectively. With this information, a graph relating the mean of square signals with the flow can be generated. The respective graph is depicted in FIG. 3i. Correspondingly, a graph relating the peak-to-mean ratio of the squares to the flow can be generated. The respective graph is depicted in FIG. 3j.

While the foregoing description has been limited to the sound characteristics of the mean of square and peak-to-mean ratios of the squares, it will be understood that this procedure is equally applicable to other characteristics as well, such as the peak count.

In all the graphs relating a characteristic to the flow, there can be provided a function best fitting the obtained values. Such best fit graphs have the reference numerals 100 and 102 in FIGS. 4a and 4b, respectively. These Figures mostly correspond to FIGS. 3i and 3j described above.

These best fit functions 100, 102 can then be used to obtain a measure for the flow based on the measured characteristic.

For example, when a capsule 4 is placed in inhaler 1 and a user inhales, for one interval (e.g. of 200 ms), the mean of square characteristic may be as indicated by arrow 104 in FIG. 4a.

Simultaneously, the peak to mean ratio of the squares may be as indicated by arrow 106 in FIG. 4b. The best fit functions 100, 102 may then be used to obtain estimates for the corresponding flow. In this example, the corresponding flow estimated by means of the mean of square noise measurement would by approximately 94 l/min and the flow estimated by means of the peak to mean ratio of the squares may be approximately 84 l/min. Again, other characteristics may also be used to determine additional estimates for the flow.

These individual flow estimates can then be used to provide an overall flow estimation. In above example, one could use the average of the flow estimates to arrive at a common flow estimate of 89 l/min (however, the individual flow estimates may also be combined in a different manner, e.g. by providing different weights to the individual flow estimates).

Thus, by means of the measurement of the sound and by evaluation of its characteristics, an estimate for the flow may be obtained.

As discussed, such a flow estimate is provided for specific time intervals, e.g. for time intervals of 200 ms. This is depicted in the graph of FIG. 5. This graph shows a real flow profile of a user as the dotted line and the estimates of the flow profile as the bars having a width corresponding to the interval (which here is 200 ms).

As will be understood, e.g., by the scatter diagram of FIG. 3a, one and the same flow may yield different results as regards the different characteristics (it is again noted that all points on the scatter diagram having the same symbol correspond to the same flow). That is, the correlation between the flow and the noise characteristics may be subject to some signal noise.

Having this in mind, the bars corresponding to the estimated flow obtained by the noise characteristics in FIG. 5 may be somewhat idealized and may in reality not follow the real flow as closely as depicted in FIG. 5. However, the inhaler 1 is typically used for several times to administer medication; e.g., the inhaler 1 may be used daily or even more than once a day.

The process described above may therefore also be used several times to arrive at a plurality of estimates for the flow profiles of different breaths. That is, one may have several bar diagrams as the one depicted in FIG. 5. Such bar diagrams may then be combined to arrive at an estimate for an average breath profile—that is, for different bar diagrams, the estimates for the first intervals (e.g. from 0 ms to 200 ms) may be combined, the estimates for the second intervals (e..g from 200 ms to 400 ms) may be combined etc.

Some results of the performance of an exemplary embodiment of the present invention will now be described with reference to the Figs. FIG. 6 depicts the number of positive blocks obtained by the present technology on the x-coordinate and the actual and measured inhaling duration on the y-coordinate. Positive blocks are those blocks (=intervals), where the detected noise exceeds a predefined threshold. That is, positive blocks indicate a spinning capsule. The graph of FIG. 6 was obtained as follows: A patient used the present inhaler 1. Another person measured the actual inhaling duration (see y-coordinate) by observing the patient. The number of positive blocks (i.e. positive intervals) was then plotted against the actual inhaling duration. As described, each interval or block has a duration of 200 ms. That is, e.g., 5 positive blocks correspond to an estimated inhaling duration of 1 s. As will be apparent, the present invention estimates inhaling durations of 1 s (corresponding to 5 positive blocks) for actual inhaling durations between approximately 0.7 s and 1.4 s.

Figure 7A:
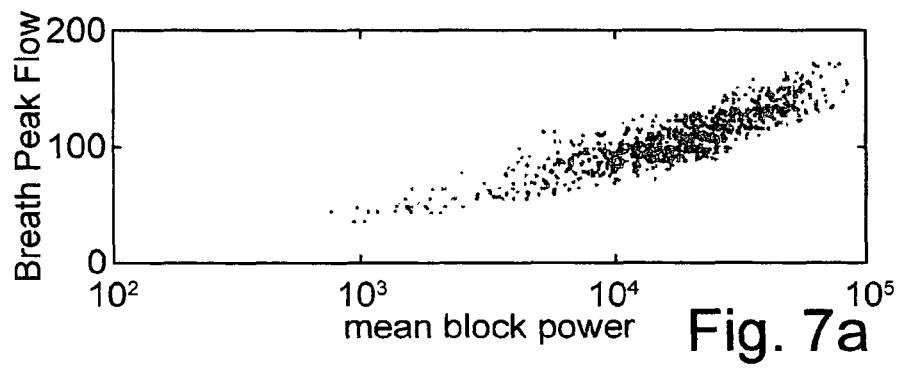
Figure 7B:
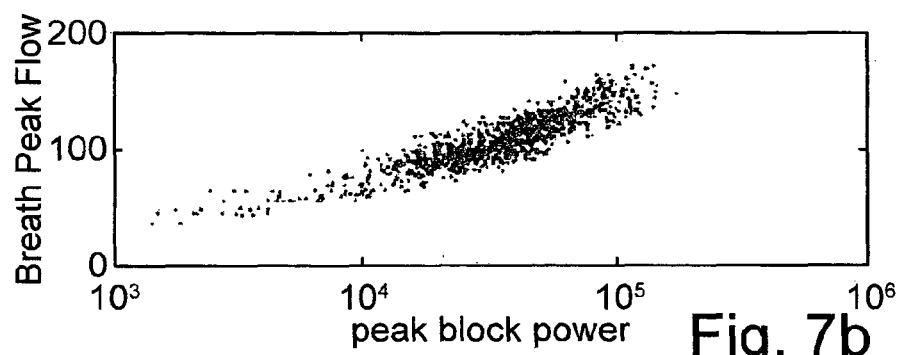
Figure 7C:
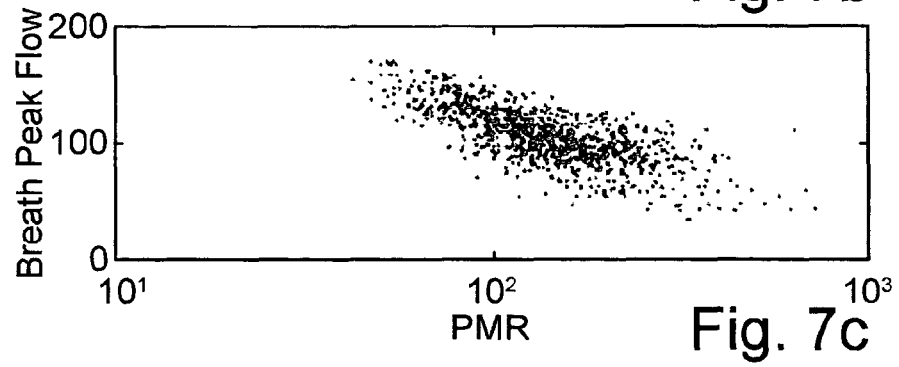

Further tests were performed with a Si-Plan® breath simulator connected to the inhaler 1. By means of this breathing simulator, it is possible to supply the inhaler 1 with a defined and known breath profile. By means of this set up, different inhalation flow features were plotted against different characteristics of the sound. Again, the sound signal was divided into different intervals or blocks (having a length of 200 ms). The algorithm first checks whether a capsule is present in the inhaler. This check is positive when the sound signal exceeds a threshold for at least 4 of 5 time intervals. If the algorithm detects the presence of a capsule, the inhalation flow features may be plotted against the characteristics of the sound. FIGS. 7a to 7c each show the breath peak flow (in l/min) on the y-coordinate. This corresponds to the maximum flow during one inhalation. On the x-coordinates are plotted the mean block power, the peak block power and the peak to mean ratio, respectively (for FIGS. 7a, 7b and 7c). The mean block power is a measure for the average signal during the inhalation, the peak block power corresponds to the highest signal during the inhalation and the peak to mean ratio corresponds is the peak signal divided by the mean signal during one inhalation. As will be appreciated, the mean block power and the peak block power have a reasonable good correlation with the actual peak flow rate and may be used to measure this peak flow rate.

Figure 7D:
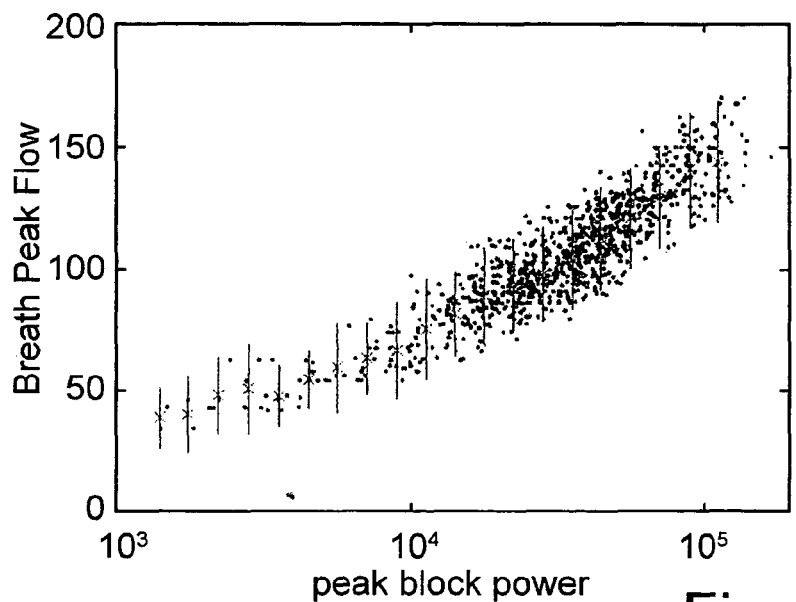

This is also shown in FIG. 7d, which depicts the 95% confidence interval (see the bars) for the correlation between the peak block power and the peak flow rate.

Figure 8A:
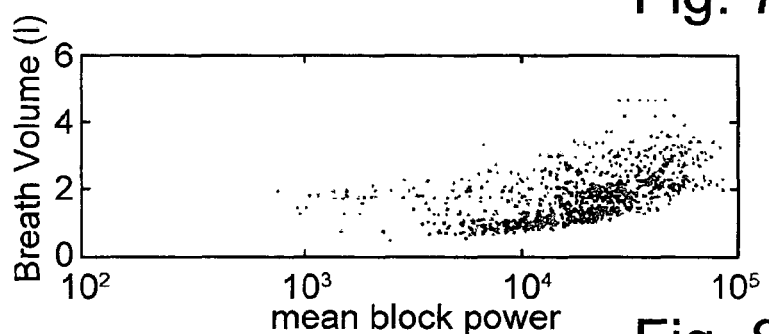
Figure 8B:
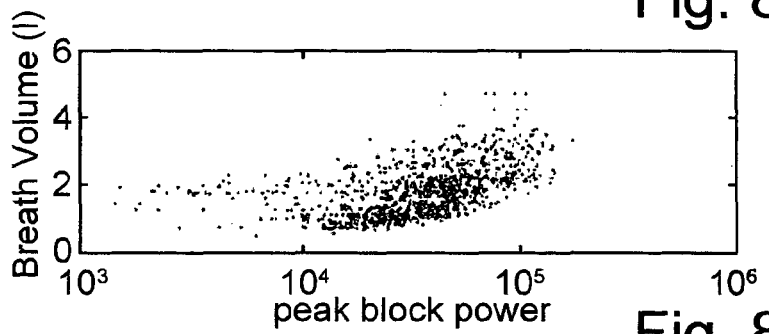
Figure 8C:
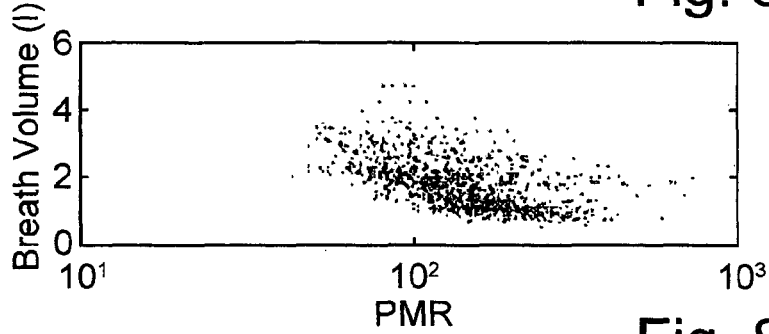
Figure 8D:
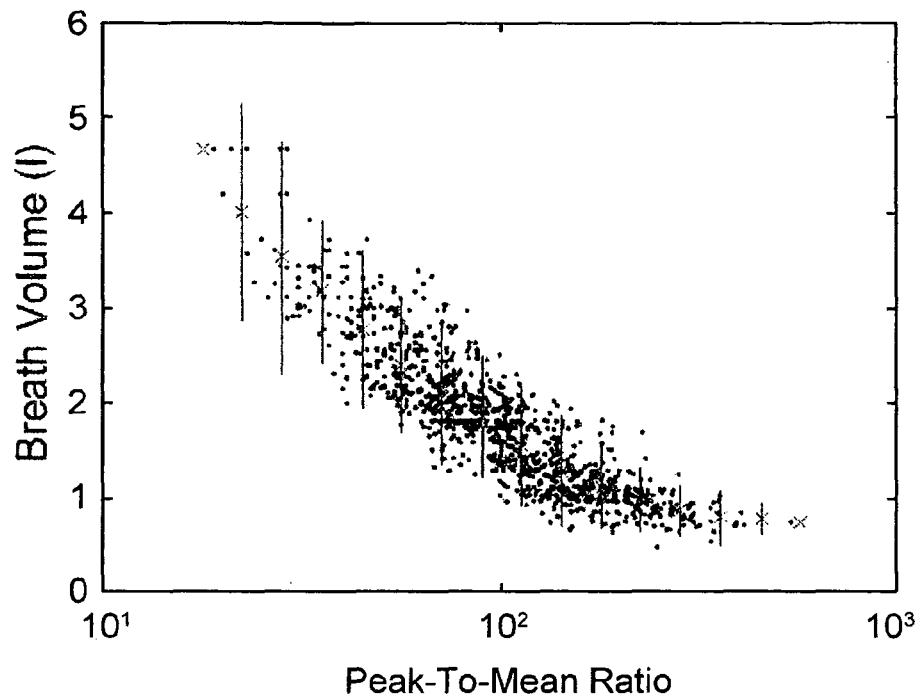

FIGS. 8a to 8c depict scatter diagrams having the described sound characteristics (i.e. mean block power, peak block power and peak to mean ratio) correlated to the breath volume (in l). It will be appreciated that the peak to mean ration has a reasonably good negative correlation with the breath volume—also see FIG. 8d in this regard, where the 95% confidence intervals for this correlation have been added as bars.

With reference to FIGS. 6a to 8c, it was described that sound characteristics were correlated to different inhalation flow features. More particularly, the inhalation flow features were inhalation duration, inhalation peak flow and inhalation volume. As will be appreciated, all these inhalation flow features are features of an entire breath (that is: of an entire inhalation). At the same time, it will be appreciated that the present technology also allows correlating the sound characteristics to instantaneous inhalation flow features, such as instantaneous flow rate (e.g., the flow rate within a respective 200 ms block) and the peak flow in a 200 ms block. Such instantaneous flow features may further be used to also obtain entire breath flow features, e.g. by integrating (to arrive at the total inhalation volume) or taking the maximum (to arrive at the inhalation peak flow).

FIG. 9 depicts the sound signal as a spectrogram. In these spectrograms, the signal strength, i.e. the signal power, is plotted as a function of frequency (in $10^4$ Hz) and time (in s). The signal power is plotted in a color code—generally, the higher the signal power, the lighter the representation in FIG. 9. The left signal corresponds to a signal of an inhalation without a capsule being present in the inhaler and the right signal corresponds to a signal of an inhalation with a capsule being present. It will be appreciated that the right signal with a capsule being present is particularly differentiated from the left signal (with no capsule being present) in the frequency region between approximately 5 kHz and approximately 10 kHz. We used the signal strength (=signal power) in this region, i.e. in the region from 5 kHz to 10 kHz to correlate it to the measured instantaneous flow rate and obtained a reasonably good fit between the third root of the signal power in this frequency band and the flow rate (see FIG. 10).

Using this approach, we measured an inhaling profile. Again, a Si-Plan® breathing simulator with a known breath profile was used and three repetitions with different inhalers were performed. This resulted in FIG. 11, which depicts the actual breath profile input from the breathing simulator and the estimates (for 200 ms intervals or blocks) provided by the present technology. It will be appreciated that the present technology provides a reasonably good estimate of the actual instantaneous flow rate.

As discussed, the present technology retrieves information as regards flow characteristics features the inhaler 1 by measuring the impacts of a capsule 4 spinning inside the inhaler 1. An exemplary flow feature is the inhalation volume. According to one embodiment (see FIG. 13), the inhaler 1 comprises a display 40, e.g., a LCD display 40, which display 40 may display the flow feature—e.g., the flow feature(s) (such as the inhalation volume of the last inhalation, the inhalation duration, the peak inhalation flow) may be displayed on the display 40.

Now referring to FIG. 12, the inhaler 1 is shown along with a computing device 354, according to one embodiment. In this embodiment, the invention also relates to a set comprising the inhaler 1 (e.g. the inhaler) and the computing device 354. That is, the inhaler 1 may comprise any of the features discussed herein. In this embodiment, the computing device 354 may comprise any computing device known in the art, such as a personal computer (PC), a mobile telephone (e.g., a smart phone (such as APPLE iPHONE, SAMSUNG GALAXY S3, S4, S5, etc.), cell phone, etc.), a tablet computer (such as an APPLE iPAD, MICROSOFT SURFACE, SAMSUNG GALAXY TAB, AMAZON KINDLE, etc.), a smart watch (e.g., MOTOROLA MOTO360, ASUS ZENWATCH, APPLE iWATCH, etc.), a laptop computer, an ultrabook computer, or a wearable device (e.g., head-up displays including GOOGLE GLASS and others, tracking and displaying devices like FITBIT). The computing device 352 is capable of communicating via one or more wireless communication technologies. Any wireless communication technology capable of receiving a signal and transmitting data to/from the inhaler 1 may be used, as would be known to one of skill in the art upon reading the present descriptions.

In one embodiment, the computing device 354 is a smart phone, as shown, capable of downloading program applications from a central application server. Any central application server may be used to download program applications, such as APPLE APP STORE, APPLE iTUNES, GOOGLE PLAY STORE, AMAZON APP STORE, etc. Any of these application servers may include a medical device application 356 (here: inhaler device application) that may be downloaded onto the computing device 354. Medical device applications may also be downloadable from servers under the control of the provider of the medical device, healthcare providers, pharmacies, hospitals, clinicians, or doctors.

In some embodiments, the inhaler 1 may be capable of communicating with the computing device 354 via a wireless communication technology. In particular, inhaler 1 may communicate with computing device 354 by means of output 32. In this regard, it is noted that output 32 may also be generally referred to as data receiving and transmitting means. That is, output 32 may be used to both transmit data and/or information to an external device (such as computing device 354) and receive data and/or information from such an external device. Any wireless communication technology may be used for transmitting the signal from the inhaler 1 to the medical device application 356, as would be known to one of skill in the art upon reading the present descriptions.

Some exemplary wireless communication technologies include, but are not limited to, Bluetooth, Bluetooth low energy (BLE), ZIGBEE, Z-WAVE, infrared (IR), WLAN such as WIFI, RF, near-field communication (NFC), and optical.

In another embodiment, a proprietary wireless communication protocol may be used to send information between the inhaler 1 and the computing device 354, with the proprietary communication protocol being configured to effectively convey information specific to the inhaler 1 and uses thereof.

In some examples, the inhaler 1 may communicate via NFC, a Bluetooth-capable implantable insulin injector, etc. In one embodiment, the inhaler 1 is an inhaler configured to communicate via BLE and/or Bluetooth.

In some further embodiments, the inhaler 1 may comprise a processor capable of executing logic, a local memory for storing data, and logic which may be accessible to the processor and/or implemented within the processor. The logic may be configured to cause the medical device to follow instructions from the computing device, send information from the inhaler 1 to the computing device 354, a networked storage device, other devices within a network, and/or a cloud, and receive information from the computing device 354, a networked storage device, other devices within a network, and/or a cloud.

The local memory of the inhaler 1 may comprise any memory known to one of skill in the art, such as RAM, ROM, non-volatile memory (NVM) such as Flash memory, removable memory such as a microSD card.

In accordance with one embodiment, a user of the computing device 354 may install a medical device application 356 on the computing device 354. The medical device application 356 may be downloaded from an application server accessible to the computing device 354, the application server being of a type known in the art. In another embodiment, the medical device application 356 may be provided to the computing device 354, for example via a computer readable storage medium, such as a CD, MicroSD card, RAM, or ROM, and/or virtually provided via a link and/or pointer that is embedded in a communication received by the computing device 354, such as a hypertext link in an email, or HTML pointer in a text message. The computing device 354 may then access the medical device application 356 via the Internet, a WLAN such as a WIFI network, a WAN, a LAN, etc., to install the medical device application 356 on the computing device 354, as would be understood by one of skill in the art upon reading the present descriptions.

That is, to summarize, the inhaler 1 may communicate with external device 354. In particular, data relating to the estimated flow profile may be communicated from the inhaler 1 to the external device 354.

As will be understood, the inhaler 1 may send data relating to the estimated flow whenever it is paired with the external device 354, that is, whenever the two devices communicate with one another. In particular, it is possible that the inhaler 1 sends the estimated flow profile of the individual breaths (i.e. of the individual instances of inhaling) to the external device 354 and the external device 354 stores the estimated flow profiles of the individual breaths and performs the further calculations (such as the combination of flow profiles of different breaths). However, as will be understood, such storing and calculation may also be performed by the inhaler 1 and more particularly by its processor.

The external device 354 may also further communicate such usage information, e.g. to healthcare providers, who can then monitor the usage of the inhaler 1 and whether or not it is used correctly.

When different method steps are described in this specification, the steps may (but do not necessarily have to) be performed in the order mentioned in this specification.

While the invention has been discussed with reference to particular embodiment, it is noted that these embodiments are not to be understood to limit the scope of the invention, which is defined by the claims.

Generally speaking, the present invention is also defined by the following aspects:

M1. A method for measuring at least one inhalation flow feature in an inhaler, wherein a capsule containing a formulation is located in the inhaler, the method comprising the steps of sensing an impact feature relating to impacts of the capsule on the inhaler and correlating the impact feature to at least one inhalation flow feature.

M2. The method according to the preceding aspect, wherein the impact feature is a sound generated by the impacts of the capsule on the inhaler.

M3. The method according to any of the preceding aspects, wherein correlating the impact feature to at least one inhalation flow feature comprises determining at least one characteristic of the sensed impact feature;

relating the at least one characteristic of the sensed impact feature to at least one inhalation flow feature.

One non-limiting example of an inhalation flow feature is an instantaneous inhalation flow.

M4. The method according to the preceding aspect, wherein the at least one characteristic comprises at least one of a mean value of the impact feature, a peak value of the impact feature and a duration of the impact feature above a threshold.

M5. The method according to the preceding aspect, wherein the at least one characteristic comprises two or three of the characteristics listed in the preceding aspect and wherein at least one inhalation flow feature is determined by a combination of the characteristics.

M6. The method according to any of the three preceding aspects, wherein the at least one characteristic comprises at least one of a peak to mean value of the impact feature, a peak count of the impact feature, a variance of the impact feature and a kurtosis of the impact feature.

M7. The method according to the preceding aspect, wherein the at least one characteristic comprises two, three or four of the characteristics listed in the preceding aspect and wherein at least one inhalation flow feature is determined by a combination of the characteristics.

M8. The method according to any of the preceding aspects with the features of aspect M3, wherein correlating the impact feature to at least one inhalation flow feature comprises dividing the sensed impact feature into time intervals, determining the at least one characteristic of the sensed impact feature for the time intervals, relating the at least one characteristic of the sensed impact feature to a flow for each time interval.

M9. The method according to the preceding aspect, wherein the steps of sensing an impact feature and correlating the impact feature to at least one inhalation flow feature with its sub-steps are performed for a plurality of inhalations, to thereby arrive at a plurality of flows for each time interval, wherein the plurality of flows for each time interval are combined to a combined flow for each time interval.

M10. The method according to the preceding aspect, wherein the plurality of inhalations is at least 3, preferably at least 5 and more preferably at least 10 inhalations.

M11. The method according to any of the preceding aspects, wherein the at least one inhalation flow feature comprises at least one of a peak inhalation flow, an inhalation flow duration and an inhalation flow volume.

M12. The method according to the preceding aspect, wherein the at least one inhalation flow feature comprises two or three of the features listed in the preceding aspect.

M13. The method according to any of the preceding aspects, wherein the at least one inhalation flow feature is displayed on the inhaler.

M14. The method according to any of the preceding aspects, wherein the method comprises sending data relating to the impact feature or the at least one inhalation flow feature to a device external to the inhaler.

M15. The method according to the preceding aspect, wherein the step of correlating the impact feature to at least one inhalation flow feature is at least partially performed by the external device.

M16. The method according to any of the aspects M1 to M14, wherein the step of correlating the impact feature to at least one inhalation flow feature is performed by the inhaler.

M17. The method according to any of the preceding aspects and further comprising the step of frequency filtering the impact feature before correlating the impact feature to at least one inhalation flow feature, wherein the filtering preferably prevents signals in the frequency range below 3 kHz and above 15 kHz to pass and further preferably, wherein the filtering prevents signals below 4.5 kHz and above 10 kHz to pass.

M18. The method according to any of the preceding aspects, the method also comprising effecting the capsule to spin in the inhaler and to impact on the inhaler.

U1 Use of the method according to any of the preceding aspects, wherein the method is performed at least partially simultaneously with the formulation being supplied to a user of the inhaler.

U2. Use of the method according to any of the preceding method aspects (denoted by an "M"), the use comprising considering the at least one inhalation flow feature to monitor the user's compliance.

U3. Use of the method according to any of the preceding method aspects, the use comprising considering the at least one inhalation flow feature to monitor a health condition of the user.

U4. Use according to any of the two preceding aspects, wherein the at least one inhalation flow feature is considered for a plurality of inhalations.

A1. An inhaler adapted to aerosolize a formulation contained in a capsule, wherein the inhaler comprises a sensor for sensing an impact feature relating to impacts of the capsule on the inhaler and a processor for correlating the impact feature to at least one inhalation flow feature.

A2. The inhaler according to the preceding aspect, wherein the sensor is a microphone.

A3. The inhaler according to any of the preceding apparatus aspects (denoted by an "A"), wherein the processor is adapted to carry out any of the steps set out in the aspects M3 to M12 and M17.

A4. The inhaler according to any of the preceding apparatus aspects, wherein the inhaler comprises a data-receiving-transmitting means to receive and transmit data from and to an external device.

A5. The inhaler according to any of the preceding apparatus aspects, wherein the sensor is fixedly mounted to the inhaler.

S1. A system comprising an inhaler adapted to aerosolize a formulation contained in a capsule and a computing device external of the inhaler, wherein the inhaler comprises a sensor for sensing an impact feature relating to impacts of the capsule on the inhaler and a data-receiving-transmitting means to receive and transmit data from and to the external computing device, wherein the external computing device also comprises data-receiving-transmitting means to receive and transmit data from and to the inhaler, wherein the inhaler and/or the external computing device comprises processing means for correlating the impact feature to at least one inhalation flow feature.

S2. The system according to the preceding aspect, wherein the sensor is a microphone.

S3. The system according to any of the preceding system aspects (denoted by an "S"), wherein the processing means is adapted to carry out any of the steps set out in the aspects M3 to M12 and M17.

The invention claimed is:

1. A method for measuring at least one inhalation flow feature in an inhaler, wherein a capsule containing a formulation is located in the inhaler, the method comprising:

sensing an impact feature relating to impacts of the capsule on the inhaler during a single inhalation, dividing the sensed impact feature into time intervals within the single inhalation, determining a mean value of the sensed impact feature for the time intervals, correlating the mean value of the sensed impact feature to an inhalation flow volume for each of the time intervals, determining a peak-to-mean ratio of the sensed impact feature for the time intervals, and correlating the peak-to-mean ratio of the sensed impact feature to an inhalation flow volume.

2. The method according to claim 1, wherein the impact feature is a sound generated by the impacts of the capsule on the inhaler.

3. The method according to claim 1, wherein the sensing the impact feature and the correlating the mean value of the sensed impact feature are performed for a plurality of inhalations.

4. The method according to claim 1, further comprising combining the inhalation flow volumes for each of the time intervals to determine an overall inhalation flow volume.

5. The method according to claim 4, wherein combining the inhalation flow volumes for each of the time intervals includes averaging the inhalation flow volumes for each of the time intervals.

6. The method according to claim 4, wherein combining the inhalation flow volumes for each of the time intervals includes providing different weights to the inhalation flow volumes for each of the time intervals.

7. The method according to claim 1, wherein each of the time intervals has a predetermined duration.

8. The method according to claim 1, wherein correlating the mean value of the sensed impact feature to the inhalation flow volume for each of the time intervals is performed after confirming, via a processor, that the capsule is located in the inhaler.

9. The method according to claim 1, wherein sensing the impact feature is performed continuously during multiple inhalations.

10. An inhaler adapted to aerosolize a formulation contained in a capsule, wherein the inhaler comprises:
    a sensor adapted to sense an impact feature relating to impacts of the capsule on the inhaler during a single inhalation, and
    a processor adapted to divide the sensed impact feature into time intervals within the single inhalation, wherein the processor is adapted to determine a mean value of the impact feature for the time intervals, wherein the processor is adapted to correlate the mean value of the impact feature to an inhalation flow volume for each of the time intervals, wherein the processor is adapted to determine a peak-to-mean ratio of the impact feature for the time intervals, and wherein the processor is adapted to correlate the peak-to-mean ratio of the impact feature to an inhalation flow volume.

11. The inhaler according to claim 10, wherein the sensor is a microphone.

12. The inhaler according to claim 10, wherein the inhaler comprises a data-receiving-transmitting means to receive and transmit data from and to an external device.

13. A system comprising an inhaler according to claim 10 and an external computing device external to the inhaler, wherein the inhaler comprises a data-receiving-transmitting means to receive and transmit data from and to the external computing device, wherein the external computing device also comprises data-receiving-transmitting means to receive and transmit data from and to the inhaler.

14. A method for measuring at least one inhalation flow feature in an inhaler, wherein a capsule containing a formulation is located in the inhaler, the method comprising:
    sensing an impact feature relating to impacts of the capsule on the inhaler,
    determining over an interval of time a mean value of the impact feature, and
    correlating the mean value of the impact feature to an inhalation flow volume over the interval of time,
    determining over the interval of time a peak-to-mean ratio of the impact feature, and
    correlating the peak-to-mean value of the impact feature to an inhalation flow volume.

15. The method according to claim 14, wherein the inhalation flow volume correlated from the mean value of the impact feature and the flow volume correlated from the peak-to-mean ratio are averaged.

16. An inhaler adapted to aerosolize a formulation contained in a capsule, wherein the inhaler comprises:
    a sensor adapted to sense an impact feature relating to impacts of the capsule on the inhaler, and
    a processor adapted to determine over an interval of time a mean value of the impact feature and wherein the processor is adapted to correlate the mean value of the impact feature to an inhalation flow volume over the interval of time, wherein the processor is further adapted to determine over the interval of time a peak-to-mean ratio of the impact feature and to correlate the peak-to-mean value of the impact feature to an inhalation flow volume.

17. The inhaler according to claim 16, wherein the processor is adapted to average the inhalation flow volume correlated from the mean value of the impact feature and the flow volume correlated from the peak-to-mean ratio.

\* \* \* \* \*